(12) United States Patent
Eisinger et al.

(10) Patent No.: US 11,660,091 B2
(45) Date of Patent: May 30, 2023

(54) SURGICAL DEVICE WITH SEAL ASSEMBLY

(71) Applicant: Covidien LP, Mansfield, MA (US)

(72) Inventors: Joseph Eisinger, Northford, CT (US); David E. Valentine, Jr., Hamden, CT (US); Ramiro D. Cabrera, Cheshire, CT (US); Stephen R. Paul, Burlington, CT (US); Patrick D. Mozdzierz, Glastonbury, CT (US); Jorge L. Boyd, East Hartford, CT (US); Anthony Sgroi, Jr., Wallingford, CT (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 17/400,285

(22) Filed: Aug. 12, 2021

(65) Prior Publication Data

US 2022/0071627 A1    Mar. 10, 2022

Related U.S. Application Data

(60) Provisional application No. 63/075,349, filed on Sep. 8, 2020.

(51) Int. Cl.
*A61B 17/068* (2006.01)
*A61B 17/072* (2006.01)
(Continued)

(52) U.S. Cl.
CPC ........ *A61B 17/0686* (2013.01); *A61B 17/072* (2013.01); *A61B 17/3417* (2013.01);
(Continued)

(58) Field of Classification Search
CPC .............. A61B 17/115; A61B 17/1155; A61B 17/0686; A61B 17/072;
(Continued)

(56) References Cited

U.S. PATENT DOCUMENTS 2,957,353 A   10/1960   Babacz
3,111,328 A   11/1963   Di Rito et al.
(Continued)

FOREIGN PATENT DOCUMENTS

CA    2451558 A1    1/2003
CN    1547454 A    11/2004
(Continued)

OTHER PUBLICATIONS

Extended European Search Report corresponding to International Application No. EP 14 18 4882.0 dated May 12, 2015.
(Continued)

*Primary Examiner* — Stephen F. Gerrity
*Assistant Examiner* — Linda J Hodge
(74) *Attorney, Agent, or Firm* — Carter, DeLuca & Farrell LLP

(57) ABSTRACT

A surgical device including a handle assembly, an elongated portion, and outer band assembly, and inner band assembly, a trocar assembly, and a seal assembly is disclosed. At least a portion of the outer band assembly is disposed radially within the outer sleeve. At least a portion of the trocar assembly is disposed radially within the inner band assembly. The seal assembly includes a first annular seal and a second annular seal. The first annular seal is disposed radially inward of the outer sleeve and radially outward of the outer band assembly. The second annular seal is disposed radially inward of the outer band assembly and radially outward of the inner band assembly.

17 Claims, 11 Drawing Sheets

(51) Int. Cl.
*A61B 17/34* (2006.01)
*A61B 34/30* (2016.01)

(52) U.S. Cl.
CPC .... *A61B 34/30* (2016.02); *A61B 2017/07257* (2013.01); *A61B 2017/07271* (2013.01); *A61B 2017/07285* (2013.01); *A61B 2017/3419* (2013.01)

(58) Field of Classification Search
CPC .......... A61B 2017/07257; A61B 2017/07271; A61B 2017/07285; A61B 2017/3419; A61B 34/30; A61B 17/3417; F16J 15/344
See application file for complete search history.

(56) References Cited

U.S. PATENT DOCUMENTS

| | | |
|---|---|---|
| 3,695,058 A | 10/1972 | Keith, Jr. |
| 3,734,515 A | 5/1973 | Dudek |
| 3,759,336 A | 9/1973 | Marcovitz et al. |
| 4,162,399 A | 7/1979 | Hudson |
| 4,606,343 A | 8/1986 | Conta et al. |
| 4,705,038 A | 11/1987 | Sjostrom et al. |
| 4,722,685 A | 2/1988 | de Estrada et al. |
| 4,823,807 A | 4/1989 | Russell et al. |
| 4,874,181 A | 10/1989 | Hsu |
| 5,129,118 A | 7/1992 | Walmesley |
| 5,129,570 A | 7/1992 | Schulze et al. |
| 5,152,744 A | 10/1992 | Krause et al. |
| 5,301,061 A | 4/1994 | Nakada et al. |
| 5,312,023 A | 5/1994 | Green et al. |
| 5,326,013 A | 7/1994 | Green et al. |
| 5,350,355 A | 9/1994 | Sklar |
| 5,383,874 A | 1/1995 | Jackson et al. |
| 5,383,880 A | 1/1995 | Hooven |
| 5,389,098 A | 2/1995 | Tsuruta et al. |
| 5,395,033 A | 3/1995 | Byrne et al. |
| 5,400,267 A | 3/1995 | Denen et al. |
| 5,411,508 A | 5/1995 | Bessler et al. |
| 5,413,267 A | 5/1995 | Solyntjes et al. |
| 5,427,087 A | 6/1995 | Ito et al. |
| 5,433,721 A | 7/1995 | Hooven et al. |
| 5,467,911 A | 11/1995 | Tsuruta et al. |
| 5,476,379 A | 12/1995 | Disel |
| 5,487,499 A | 1/1996 | Sorrentino et al. |
| 5,518,163 A | 5/1996 | Hooven |
| 5,518,164 A | 5/1996 | Hooven |
| 5,526,822 A | 6/1996 | Burbank et al. |
| 5,529,235 A | 6/1996 | Boiarski et al. |
| 5,535,934 A | 7/1996 | Boiarski et al. |
| 5,535,937 A | 7/1996 | Boiarski et al. |
| 5,540,375 A | 7/1996 | Bolanos et al. |
| 5,540,706 A | 7/1996 | Aust et al. |
| 5,542,594 A | 8/1996 | McKean et al. |
| 5,549,637 A | 8/1996 | Crainich |
| 5,553,675 A | 9/1996 | Pitzen et al. |
| 5,562,239 A | 10/1996 | Boiarski et al. |
| 5,564,615 A | 10/1996 | Bishop et al. |
| 5,609,560 A | 3/1997 | Ichikawa et al. |
| 5,626,587 A | 5/1997 | Bishop et al. |
| 5,632,432 A | 5/1997 | Schulze et al. |
| 5,645,209 A | 7/1997 | Green et al. |
| 5,647,526 A | 7/1997 | Green et al. |
| 5,653,374 A | 8/1997 | Young et al. |
| 5,658,300 A | 8/1997 | Bito et al. |
| 5,662,662 A | 9/1997 | Bishop et al. |
| 5,667,517 A | 9/1997 | Hooven |
| 5,693,042 A | 12/1997 | Boiarski et al. |
| 5,704,534 A | 1/1998 | Huitema et al. |
| 5,713,505 A | 2/1998 | Huitema |
| 5,762,603 A | 6/1998 | Thompson |
| 5,779,130 A | 7/1998 | Alesi et al. |
| 5,782,396 A | 7/1998 | Mastri et al. |
| 5,782,397 A | 7/1998 | Koukline |
| 5,792,573 A | 8/1998 | Pitzen et al. |
| 5,797,536 A | 8/1998 | Smith et al. |
| 5,820,009 A | 10/1998 | Melling et al. |
| 5,863,159 A | 1/1999 | Lasko |
| 5,865,361 A | 2/1999 | Milliman et al. |
| 5,908,427 A | 6/1999 | McKean et al. |
| 5,954,259 A | 9/1999 | Viola et al. |
| 5,964,774 A | 10/1999 | McKean et al. |
| 5,993,454 A | 11/1999 | Longo |
| 6,010,054 A | 1/2000 | Johnson et al. |
| 6,017,354 A | 1/2000 | Culp et al. |
| 6,032,849 A | 3/2000 | Mastri et al. |
| 6,045,560 A | 4/2000 | McKean et al. |
| 6,090,123 A | 7/2000 | Culp et al. |
| 6,126,651 A | 10/2000 | Mayer |
| 6,129,547 A | 10/2000 | Cise et al. |
| 6,165,169 A | 12/2000 | Panescu et al. |
| 6,239,732 B1 | 5/2001 | Cusey |
| 6,241,139 B1 | 6/2001 | Milliman et al. |
| 6,264,086 B1 | 7/2001 | McGuckin, Jr. |
| 6,264,087 B1 | 7/2001 | Whitman |
| 6,302,311 B1 | 10/2001 | Adams et al. |
| 6,315,184 B1 | 11/2001 | Whitman |
| 6,321,855 B1 | 11/2001 | Barnes |
| 6,329,778 B1 | 12/2001 | Culp et al. |
| 6,343,731 B1 | 2/2002 | Adams et al. |
| 6,348,061 B1 | 2/2002 | Whitman |
| 6,368,324 B1 | 4/2002 | Dinger et al. |
| 6,371,909 B1 | 4/2002 | Hoeg et al. |
| 6,434,507 B1 | 8/2002 | Clayton et al. |
| 6,443,973 B1 | 9/2002 | Whitman |
| 6,461,372 B1 | 10/2002 | Jensen et al. |
| 6,488,197 B1 | 12/2002 | Whitman |
| 6,491,201 B1 | 12/2002 | Whitman |
| 6,533,157 B1 | 3/2003 | Whitman |
| 6,537,280 B2 | 3/2003 | Dinger et al. |
| 6,610,066 B2 | 8/2003 | Dinger et al. |
| 6,611,793 B1 | 8/2003 | Burnside et al. |
| 6,645,218 B1 | 11/2003 | Cassidy et al. |
| 6,654,999 B2 | 12/2003 | Stoddard et al. |
| 6,698,643 B2 | 3/2004 | Whitman |
| 6,699,177 B1 | 3/2004 | Wang et al. |
| 6,716,233 B1 | 4/2004 | Whitman |
| 6,743,240 B2 | 6/2004 | Smith et al. |
| 6,783,533 B2 | 8/2004 | Green et al. |
| 6,792,390 B1 | 9/2004 | Burnside et al. |
| 6,793,652 B1 | 9/2004 | Whitman et al. |
| 6,817,508 B1 | 11/2004 | Racenet et al. |
| 6,830,174 B2 | 12/2004 | Hillstead et al. |
| 6,846,308 B2 | 1/2005 | Whitman et al. |
| 6,846,309 B2 | 1/2005 | Whitman et al. |
| 6,849,071 B2 | 2/2005 | Whitman et al. |
| 6,860,892 B1 | 3/2005 | Tanaka et al. |
| 6,899,538 B2 | 5/2005 | Matoba |
| 6,905,057 B2 | 6/2005 | Swayze et al. |
| 6,959,852 B2 | 11/2005 | Shelton, IV et al. |
| 6,964,363 B2 | 11/2005 | Wales et al. |
| 6,981,628 B2 | 1/2006 | Wales |
| 6,981,941 B2 | 1/2006 | Whitman et al. |
| 6,986,451 B1 | 1/2006 | Mastri et al. |
| 6,988,649 B2 | 1/2006 | Shelton, IV et al. |
| 7,032,798 B2 | 4/2006 | Whitman et al. |
| RE39,152 E | 6/2006 | Aust et al. |
| 7,055,731 B2 | 6/2006 | Shelton, IV et al. |
| 7,059,508 B2 | 6/2006 | Shelton, IV et al. |
| 7,077,856 B2 | 7/2006 | Whitman |
| 7,111,769 B2 | 9/2006 | Wales et al. |
| 7,122,029 B2 | 10/2006 | Koop et al. |
| 7,140,528 B2 | 11/2006 | Shelton, IV |
| 7,141,049 B2 | 11/2006 | Stern et al. |
| 7,143,923 B2 | 12/2006 | Shelton, IV et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,172,104 B2 | 2/2007 | Scirica et al. |
| 7,225,964 B2 | 6/2007 | Mastri et al. |
| 7,238,021 B1 | 7/2007 | Johnson |
| 7,246,734 B2 | 7/2007 | Shelton, IV |
| 7,252,660 B2 | 8/2007 | Kunz |
| 7,328,828 B2 | 2/2008 | Ortiz et al. |

(56) References Cited

U.S. PATENT DOCUMENTS

| | | |
|---|---|---|
| 7,364,061 B2 | 4/2008 | Swayze et al. |
| 7,380,695 B2 | 6/2008 | Doll et al. |
| 7,380,696 B2 | 6/2008 | Shelton, IV et al. |
| 7,404,508 B2 | 7/2008 | Smith et al. |
| 7,407,078 B2 | 8/2008 | Shelton, IV et al. |
| 7,416,101 B2 | 8/2008 | Shelton, IV et al. |
| 7,419,080 B2 | 9/2008 | Smith et al. |
| 7,422,139 B2 | 9/2008 | Shelton, IV et al. |
| 7,431,189 B2 | 10/2008 | Shelton, IV et al. |
| 7,441,684 B2 | 10/2008 | Shelton, IV et al. |
| 7,448,525 B2 | 11/2008 | Shelton, IV et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,481,347 B2 | 1/2009 | Roy |
| 7,481,824 B2 | 1/2009 | Boudreaux et al. |
| 7,487,899 B2 | 2/2009 | Shelton, IV et al. |
| 7,549,564 B2 | 6/2009 | Boudreaux |
| 7,565,993 B2 | 7/2009 | Milliman et al. |
| 7,568,603 B2 | 8/2009 | Shelton, IV et al. |
| 7,575,144 B2 | 8/2009 | Ortiz et al. |
| 7,588,175 B2 | 9/2009 | Timm et al. |
| 7,588,176 B2 | 9/2009 | Timm et al. |
| 7,637,409 B2 | 12/2009 | Marczyk |
| 7,641,093 B2 | 1/2010 | Doll et al. |
| 7,644,848 B2 | 1/2010 | Swayze et al. |
| 7,670,334 B2 | 3/2010 | Hueil et al. |
| 7,673,780 B2 | 3/2010 | Shelton, IV et al. |
| 7,699,835 B2 | 4/2010 | Lee et al. |
| 7,721,931 B2 | 5/2010 | Shelton, IV et al. |
| 7,738,971 B2 | 6/2010 | Swayze et al. |
| 7,740,159 B2 | 6/2010 | Shelton, IV et al. |
| 7,743,960 B2 | 6/2010 | Whitman et al. |
| 7,758,613 B2 | 7/2010 | Whitman |
| 7,766,210 B2 | 8/2010 | Shelton, IV et al. |
| 7,770,773 B2 | 8/2010 | Whitman et al. |
| 7,770,775 B2 | 8/2010 | Shelton, IV et al. |
| 7,793,812 B2 | 9/2010 | Moore et al. |
| 7,799,039 B2 | 9/2010 | Shelton, IV et al. |
| 7,802,712 B2 | 9/2010 | Milliman et al. |
| 7,803,151 B2 | 9/2010 | Whitman |
| 7,822,458 B2 | 10/2010 | Webster, III et al. |
| 7,845,534 B2 | 12/2010 | Viola et al. |
| 7,845,537 B2 | 12/2010 | Shelton, IV et al. |
| 7,857,185 B2 | 12/2010 | Swayze et al. |
| 7,870,989 B2 | 1/2011 | Viola et al. |
| 7,900,805 B2 | 3/2011 | Shelton, IV et al. |
| 7,905,897 B2 | 3/2011 | Whitman et al. |
| 7,918,230 B2 | 4/2011 | Whitman et al. |
| 7,922,061 B2 | 4/2011 | Shelton, IV et al. |
| 7,922,719 B2 | 4/2011 | Ralph et al. |
| 7,947,034 B2 | 5/2011 | Whitman |
| 7,951,071 B2 | 5/2011 | Whitman et al. |
| 7,954,682 B2 | 6/2011 | Giordano et al. |
| 7,959,051 B2 | 6/2011 | Smith et al. |
| 7,963,433 B2 | 6/2011 | Whitman et al. |
| 7,967,178 B2 | 6/2011 | Scirica et al. |
| 7,967,179 B2 | 6/2011 | Olson et al. |
| 7,992,758 B2 | 8/2011 | Whitman et al. |
| 8,011,550 B2 | 9/2011 | Aranyi et al. |
| 8,016,178 B2 | 9/2011 | Olson et al. |
| 8,016,855 B2 | 9/2011 | Whitman et al. |
| 8,020,743 B2 | 9/2011 | Shelton, IV |
| 8,025,199 B2 | 9/2011 | Whitman et al. |
| 8,035,487 B2 | 10/2011 | Malackowski |
| 8,052,024 B2 | 11/2011 | Viola et al. |
| 8,056,787 B2 | 11/2011 | Boudreaux et al. |
| 8,114,118 B2 | 2/2012 | Knodel et al. |
| 8,127,975 B2 | 3/2012 | Olson et al. |
| 8,132,705 B2 | 3/2012 | Viola et al. |
| 8,152,516 B2 | 4/2012 | Harvey et al. |
| 8,157,150 B2 | 4/2012 | Viola et al. |
| 8,157,151 B2 | 4/2012 | Ingmanson et al. |
| 8,182,494 B1 | 5/2012 | Yencho et al. |
| 8,186,555 B2 | 5/2012 | Shelton, IV et al. |
| 8,186,587 B2 | 5/2012 | Zmood et al. |
| 8,220,367 B2 | 7/2012 | Hsu |
| 8,235,273 B2 | 8/2012 | Olson et al. |
| 8,241,322 B2 | 8/2012 | Whitman et al. |
| 8,272,554 B2 | 9/2012 | Whitman et al. |
| 8,292,150 B2 | 10/2012 | Bryant |
| 8,292,888 B2 | 10/2012 | Whitman |
| 8,303,581 B2 | 11/2012 | Arts et al. |
| 8,342,379 B2 | 1/2013 | Whitman et al. |
| 8,348,130 B2 | 1/2013 | Shah et al. |
| 8,348,855 B2 | 1/2013 | Hillely et al. |
| 8,353,440 B2 | 1/2013 | Whitman et al. |
| 8,357,144 B2 | 1/2013 | Whitman et al. |
| 8,365,633 B2 | 2/2013 | Simaan et al. |
| 8,365,972 B2 | 2/2013 | Aranyi et al. |
| 8,371,492 B2 | 2/2013 | Aranyi et al. |
| 8,372,057 B2 | 2/2013 | Cude et al. |
| 8,391,957 B2 | 3/2013 | Carlson et al. |
| 8,403,926 B2 | 3/2013 | Nobis et al. |
| 8,403,949 B2 | 3/2013 | Palmer et al. |
| 8,418,904 B2 | 4/2013 | Wenchell et al. |
| 8,424,739 B2 | 4/2013 | Racenet et al. |
| 8,454,585 B2 | 6/2013 | Whitman |
| 8,505,802 B2 | 8/2013 | Viola et al. |
| 8,517,241 B2 | 8/2013 | Nicholas et al. |
| 8,523,043 B2 | 9/2013 | Ullrich et al. |
| 8,551,076 B2 | 10/2013 | Duval et al. |
| 8,561,871 B2 | 10/2013 | Rajappa et al. |
| 8,561,874 B2 | 10/2013 | Scirica |
| 8,590,763 B2 | 11/2013 | Milliman |
| 8,602,287 B2 | 12/2013 | Yates et al. |
| 8,623,000 B2 | 1/2014 | Humayun et al. |
| 8,627,995 B2 | 1/2014 | Smith et al. |
| 8,632,463 B2 | 1/2014 | Drinan et al. |
| 8,636,766 B2 | 1/2014 | Milliman et al. |
| 8,647,258 B2 | 2/2014 | Aranyi et al. |
| 8,652,121 B2 | 2/2014 | Quick et al. |
| 8,657,174 B2 | 2/2014 | Yates et al. |
| 8,657,177 B2 | 2/2014 | Scirica et al. |
| 8,672,206 B2 | 3/2014 | Aranyi et al. |
| 8,696,552 B2 | 4/2014 | Whitman |
| 8,708,213 B2 | 4/2014 | Shelton, IV et al. |
| 8,715,306 B2 | 5/2014 | Faller et al. |
| 8,752,749 B2 | 6/2014 | Moore et al. |
| 8,758,391 B2 | 6/2014 | Swayze et al. |
| 8,806,973 B2 | 8/2014 | Ross et al. |
| 8,808,311 B2 | 8/2014 | Heinrich et al. |
| 8,820,605 B2 | 9/2014 | Shelton, IV |
| 8,828,023 B2 | 9/2014 | Neff et al. |
| 8,851,355 B2 | 10/2014 | Aranyi et al. |
| 8,858,571 B2 | 10/2014 | Shelton, IV et al. |
| 8,875,972 B2 | 11/2014 | Weisenburgh, II et al. |
| 8,888,762 B2 | 11/2014 | Whitman |
| 8,893,946 B2 | 11/2014 | Boudreaux et al. |
| 8,899,462 B2 | 12/2014 | Kostrzewski et al. |
| 8,905,289 B2 | 12/2014 | Patel et al. |
| 8,919,630 B2 | 12/2014 | Milliman |
| 8,931,680 B2 | 1/2015 | Milliman |
| 8,939,344 B2 | 1/2015 | Olson et al. |
| 8,950,646 B2 | 2/2015 | Viola |
| 8,960,519 B2 | 2/2015 | Whitman et al. |
| 8,961,396 B2 | 2/2015 | Azarbarzin et al. |
| 8,967,443 B2 | 3/2015 | McCuen |
| 8,968,276 B2 | 3/2015 | Zemlok et al. |
| 8,968,337 B2 | 3/2015 | Whitfield et al. |
| 8,992,422 B2 | 3/2015 | Spivey et al. |
| 9,016,545 B2 | 4/2015 | Aranyi et al. |
| 9,023,014 B2 | 5/2015 | Chowaniec et al. |
| 9,033,868 B2 | 5/2015 | Whitman et al. |
| 9,055,943 B2 | 6/2015 | Zemlok et al. |
| 9,064,653 B2 | 6/2015 | Prest et al. |
| 9,072,515 B2 | 7/2015 | Hall et al. |
| 9,113,847 B2 | 8/2015 | Whitman et al. |
| 9,113,875 B2 | 8/2015 | Viola et al. |
| 9,113,876 B2 | 8/2015 | Zemlok et al. |
| 9,113,899 B2 | 8/2015 | Garrison et al. |
| 9,216,013 B2 | 12/2015 | Scirica et al. |
| 9,241,712 B2 | 1/2016 | Zemlok et al. |
| 9,282,961 B2 | 3/2016 | Whitman et al. |

(56) References Cited

U.S. PATENT DOCUMENTS

| | | |
|---|---|---|
| 9,282,963 B2 | 3/2016 | Bryant |
| 9,295,522 B2 | 3/2016 | Kostrzewski |
| 9,307,986 B2 | 4/2016 | Hall et al. |
| 9,579,099 B2 | 2/2017 | Penna et al. |
| 10,463,365 B2 | 11/2019 | Williams |
| 2001/0031975 A1 | 10/2001 | Whitman et al. |
| 2002/0049454 A1 | 4/2002 | Whitman et al. |
| 2002/0165541 A1 | 11/2002 | Whitman |
| 2003/0038938 A1 | 2/2003 | Jung et al. |
| 2003/0165794 A1 | 9/2003 | Matoba |
| 2004/0034369 A1 | 2/2004 | Sauer et al. |
| 2004/0111012 A1 | 6/2004 | Whitman |
| 2004/0133189 A1 | 7/2004 | Sakurai |
| 2004/0153124 A1 | 8/2004 | Whitman |
| 2004/0176751 A1 | 9/2004 | Weitzner et al. |
| 2004/0193146 A1 | 9/2004 | Lee et al. |
| 2005/0125027 A1 | 6/2005 | Knodel et al. |
| 2005/0131442 A1 | 6/2005 | Yachia et al. |
| 2006/0142656 A1 | 6/2006 | Malackowski et al. |
| 2006/0142740 A1 | 6/2006 | Sherman et al. |
| 2006/0142744 A1 | 6/2006 | Boutoussov |
| 2006/0259073 A1 | 11/2006 | Miyamoto et al. |
| 2006/0278680 A1 | 12/2006 | Viola et al. |
| 2006/0284730 A1 | 12/2006 | Schmid et al. |
| 2007/0023476 A1 | 2/2007 | Whitman et al. |
| 2007/0023477 A1 | 2/2007 | Whitman et al. |
| 2007/0027469 A1 | 2/2007 | Smith et al. |
| 2007/0029363 A1 | 2/2007 | Popov |
| 2007/0084897 A1 | 4/2007 | Shelton et al. |
| 2007/0102472 A1 | 5/2007 | Shelton |
| 2007/0152014 A1 | 7/2007 | Gillum et al. |
| 2007/0175947 A1 | 8/2007 | Ortiz et al. |
| 2007/0175949 A1 | 8/2007 | Shelton et al. |
| 2007/0175950 A1 | 8/2007 | Shelton et al. |
| 2007/0175951 A1 | 8/2007 | Shelton et al. |
| 2007/0175955 A1 | 8/2007 | Shelton et al. |
| 2007/0219571 A1* | 9/2007 | Balbierz ............ A61B 17/1155 606/153 |
| 2007/0270784 A1 | 11/2007 | Smith et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0058801 A1 | 3/2008 | Taylor et al. |
| 2008/0109012 A1 | 5/2008 | Falco et al. |
| 2008/0110958 A1 | 5/2008 | McKenna et al. |
| 2008/0147089 A1 | 6/2008 | Loh et al. |
| 2008/0167736 A1 | 7/2008 | Swayze et al. |
| 2008/0185419 A1 | 8/2008 | Smith et al. |
| 2008/0188841 A1 | 8/2008 | Tomasello et al. |
| 2008/0197167 A1 | 8/2008 | Viola et al. |
| 2008/0208195 A1 | 8/2008 | Shores et al. |
| 2008/0237296 A1 | 10/2008 | Boudreaux et al. |
| 2008/0251561 A1 | 10/2008 | Eades et al. |
| 2008/0255413 A1 | 10/2008 | Zemlok et al. |
| 2008/0255607 A1 | 10/2008 | Zemlok |
| 2008/0262654 A1 | 10/2008 | Omori et al. |
| 2008/0308603 A1 | 12/2008 | Shelton et al. |
| 2009/0012533 A1 | 1/2009 | Barbagli et al. |
| 2009/0090763 A1 | 4/2009 | Zemlok et al. |
| 2009/0099876 A1 | 4/2009 | Whitman |
| 2009/0138006 A1 | 5/2009 | Bales et al. |
| 2009/0171147 A1 | 7/2009 | Lee et al. |
| 2009/0182193 A1 | 7/2009 | Whitman et al. |
| 2009/0209946 A1 | 8/2009 | Swayze et al. |
| 2009/0209990 A1 | 8/2009 | Yates et al. |
| 2009/0254094 A1 | 10/2009 | Knapp et al. |
| 2009/0299141 A1 | 12/2009 | Downey et al. |
| 2010/0023022 A1 | 1/2010 | Zeiner et al. |
| 2010/0069942 A1 | 3/2010 | Shelton, IV |
| 2010/0193568 A1 | 8/2010 | Scheib et al. |
| 2010/0211053 A1 | 8/2010 | Ross et al. |
| 2010/0225073 A1 | 9/2010 | Porter et al. |
| 2011/0006101 A1 | 1/2011 | Hall et al. |
| 2011/0017801 A1 | 1/2011 | Zemlok et al. |
| 2011/0071508 A1 | 3/2011 | Duval et al. |
| 2011/0077673 A1 | 3/2011 | Grubac et al. |
| 2011/0121049 A1 | 5/2011 | Malinouskas et al. |
| 2011/0125138 A1 | 5/2011 | Malinouskas et al. |
| 2011/0139851 A1 | 6/2011 | McCuen |
| 2011/0155783 A1 | 6/2011 | Rajappa et al. |
| 2011/0155786 A1 | 6/2011 | Shelton, IV |
| 2011/0172648 A1 | 7/2011 | Jeong |
| 2011/0174009 A1 | 7/2011 | Iizuka et al. |
| 2011/0174099 A1 | 7/2011 | Ross et al. |
| 2011/0184245 A1 | 7/2011 | Xia et al. |
| 2011/0204119 A1 | 8/2011 | McCuen |
| 2011/0218522 A1 | 9/2011 | Whitman |
| 2011/0276057 A1 | 11/2011 | Conlon et al. |
| 2011/0290854 A1 | 12/2011 | Timm et al. |
| 2011/0295242 A1 | 12/2011 | Spivey et al. |
| 2011/0295269 A1 | 12/2011 | Swensgard et al. |
| 2012/0000962 A1 | 1/2012 | Racenet et al. |
| 2012/0074199 A1 | 3/2012 | Olson et al. |
| 2012/0089131 A1 | 4/2012 | Zemlok et al. |
| 2012/0104071 A1 | 5/2012 | Bryant |
| 2012/0116368 A1 | 5/2012 | Viola |
| 2012/0143002 A1 | 6/2012 | Aranyi et al. |
| 2012/0172924 A1 | 7/2012 | Allen, IV |
| 2012/0211542 A1 | 8/2012 | Racenet |
| 2012/0223121 A1 | 9/2012 | Viola et al. |
| 2012/0245428 A1 | 9/2012 | Smith et al. |
| 2012/0253329 A1 | 10/2012 | Zemlok et al. |
| 2012/0310220 A1 | 12/2012 | Malkowski et al. |
| 2012/0323226 A1 | 12/2012 | Chowaniec et al. |
| 2012/0330285 A1 | 12/2012 | Hartoumbekis et al. |
| 2013/0093149 A1 | 4/2013 | Saur et al. |
| 2013/0181035 A1 | 7/2013 | Milliman |
| 2013/0184704 A1 | 7/2013 | Beardsley et al. |
| 2013/0214025 A1 | 8/2013 | Zemlok et al. |
| 2013/0274722 A1 | 10/2013 | Kostrzewski et al. |
| 2013/0282052 A1 | 10/2013 | Aranyi et al. |
| 2013/0292451 A1 | 11/2013 | Viola et al. |
| 2013/0313304 A1 | 11/2013 | Shelton, IV et al. |
| 2013/0317486 A1 | 11/2013 | Nicholas et al. |
| 2013/0319706 A1 | 12/2013 | Nicholas et al. |
| 2013/0324978 A1 | 12/2013 | Nicholas et al. |
| 2013/0324979 A1 | 12/2013 | Nicholas et al. |
| 2013/0334281 A1 | 12/2013 | Williams |
| 2014/0012236 A1 | 1/2014 | Williams et al. |
| 2014/0012237 A1 | 1/2014 | Pribanic et al. |
| 2014/0012289 A1 | 1/2014 | Snow et al. |
| 2014/0025046 A1 | 1/2014 | Williams et al. |
| 2014/0110455 A1 | 4/2014 | Ingmanson et al. |
| 2014/0207125 A1 | 7/2014 | Applegate et al. |
| 2014/0207182 A1 | 7/2014 | Zergiebel et al. |
| 2014/0207185 A1 | 7/2014 | Goble et al. |
| 2014/0236174 A1 | 8/2014 | Williams et al. |
| 2014/0276932 A1 | 9/2014 | Williams et al. |
| 2014/0299647 A1 | 10/2014 | Scirica et al. |
| 2014/0303668 A1 | 10/2014 | Nicholas et al. |
| 2014/0358129 A1 | 12/2014 | Zergiebel et al. |
| 2014/0361068 A1 | 12/2014 | Aranyi et al. |
| 2014/0365235 A1 | 12/2014 | DeBoer et al. |
| 2014/0373652 A1 | 12/2014 | Zergiebel et al. |
| 2015/0014392 A1 | 1/2015 | Williams et al. |
| 2015/0048144 A1 | 2/2015 | Whitman |
| 2015/0076205 A1 | 3/2015 | Zergiebel |
| 2015/0080912 A1 | 3/2015 | Sapre |
| 2015/0112381 A1 | 4/2015 | Richard |
| 2015/0122870 A1 | 5/2015 | Zemlok et al. |
| 2015/0133224 A1 | 5/2015 | Whitman et al. |
| 2015/0150547 A1 | 6/2015 | Ingmanson et al. |
| 2015/0150574 A1 | 6/2015 | Richard et al. |
| 2015/0157320 A1 | 6/2015 | Zergiebel et al. |
| 2015/0157321 A1 | 6/2015 | Zergiebel et al. |
| 2015/0164502 A1 | 6/2015 | Richard et al. |
| 2015/0201931 A1 | 7/2015 | Zergiebel et al. |
| 2015/0272577 A1 | 10/2015 | Zemlok et al. |
| 2015/0297199 A1 | 10/2015 | Nicholas et al. |
| 2015/0303996 A1 | 10/2015 | Calderoni |
| 2015/0320420 A1 | 11/2015 | Penna et al. |
| 2015/0327850 A1 | 11/2015 | Kostrzewski |
| 2015/0342601 A1 | 12/2015 | Williams et al. |

(56) References Cited

U.S. PATENT DOCUMENTS

| | | | |
|---|---|---|---|
| 2015/0342603 A1 | 12/2015 | Zergiebel et al. | |
| 2015/0374366 A1 | 12/2015 | Zergiebel et al. | |
| 2015/0374370 A1 | 12/2015 | Zergiebel et al. | |
| 2015/0374371 A1 | 12/2015 | Richard et al. | |
| 2015/0374372 A1 | 12/2015 | Zergiebel et al. | |
| 2015/0374449 A1 | 12/2015 | Chowaniec et al. | |
| 2015/0380187 A1 | 12/2015 | Zergiebel et al. | |
| 2016/0095585 A1 | 4/2016 | Zergiebel et al. | |
| 2016/0095596 A1 | 4/2016 | Scirica et al. | |
| 2016/0106406 A1 | 4/2016 | Cabrera et al. | |
| 2016/0113648 A1 | 4/2016 | Zergiebel et al. | |
| 2016/0113649 A1 | 4/2016 | Zergiebel et al. | |
| 2019/0201029 A1* | 7/2019 | Shelton, IV | H01R 13/5219 |
| 2020/0214793 A1 | 7/2020 | Valentine et al. | |
| 2021/0228211 A1 | 7/2021 | Eisinger | |
| 2021/0315660 A1 | 10/2021 | Williams et al. | |

FOREIGN PATENT DOCUMENTS

| | | |
|---|---|---|
| CN | 1957854 A | 5/2007 |
| CN | 101495046 A | 7/2009 |
| CN | 101856251 A | 10/2010 |
| CN | 102247182 A | 11/2011 |
| DE | 102008053842 A1 | 5/2010 |
| EP | 0705571 A1 | 4/1996 |
| EP | 1563793 A1 | 8/2005 |
| EP | 1759652 A2 | 3/2007 |
| EP | 1769754 A1 | 4/2007 |
| EP | 1908412 A2 | 4/2008 |
| EP | 1917929 A1 | 5/2008 |
| EP | 1952769 A2 | 8/2008 |
| EP | 2090247 A1 | 8/2009 |
| EP | 2245994 A1 | 11/2010 |
| EP | 2316345 A1 | 5/2011 |
| EP | 2377472 A1 | 10/2011 |
| EP | 2668910 A2 | 12/2013 |
| EP | 2815705 A1 | 12/2014 |
| ES | 2333509 A1 | 2/2010 |
| FR | 2861574 A1 | 5/2005 |
| JP | 2005125075 A | 5/2005 |
| KR | 20120022521 A | 3/2012 |
| WO | 2011108840 A2 | 9/2011 |
| WO | 2012/040984 A1 | 4/2012 |

OTHER PUBLICATIONS

Canadian Office Action corresponding to International Application No. CA 2640399 dated May 7, 2015.
Japanese Office Action corresponding to International Application No. JP 2011-197365 dated Mar. 23, 2015.
Japanese Office Action corresponding to International Application No. JP 2011-084092 dated May 20, 2015.
Japanese Office Action corresponding to International Application No. JP 2014-148482 dated Jun. 2, 2015.
Extended European Search Report corresponding to International Application No. EP 14 18 9358.6 dated Jul. 8, 2015.
Extended European Search Report corresponding to International Application No. EP 14 19 6148.2 dated Apr. 23, 2015.
Partial European Search Report corresponding to International Application No. EP 14 19 6704.2 dated May 11, 2015.
Australian Office Action corresponding to International Application No. AU 2010241367 dated Aug. 20, 2015.
Partial European Search Report corresponding to International Application No. EP 14 19 9783.3 dated Sep. 3, 2015.
Extended European Search Report corresponding to International Application No. EP 15 16 9962.6 dated Sep. 14, 2015.
Extended European Search Report corresponding to International Application No. EP 15 15 1076.5 dated Apr. 22, 2015.
Japanese Office Action corresponding to International Application No. JP 2011-084092 dated Jan. 14, 2016.
Extended European Search Report corresponding to International Application No. EP 12 19 7970.2 dated Jan. 28, 2016.
Chinese Office Action corresponding to International Application No. CN 201210560638.1 dated Oct. 21, 2015.
European Office Action corresponding to International Application No. EP 14 15 9056.2 dated Oct. 26, 2015.
Australian Examination Report No. 1 corresponding to International Application No. AU 2015200153 dated Dec. 11, 2015.
Australian Examination Report No. 1 corresponding to International Application No. AU 2014204542 dated Jan. 7, 2016.
Chinese Office Action corresponding to International Application No. CN 201310125449.6 dated Feb. 3, 2016.
Extended European Search Report corresponding to International Application No. EP 15 19 0245.9 dated Jan. 28, 2016.
Extended European Search Report corresponding to International Application No. EP 15 16 7793.7 dated Apr. 5, 2016.
European Office Action corresponding to International Application No. EP 14 18 4882.0 dated Apr. 25, 2016.
Extended European Search Report corresponding to International Application No. EP 14 19 6704.2 dated Sep. 24, 2015.
International Search Report and Written Opinion corresponding to Int'l Appln. No. PCT/US2015/051837, dated Dec. 21, 2015.
Extended European Search Report corresponding to International Application No. EP 14 19 7563.1 dated Aug. 5, 2015.
Partial European Search Report corresponding to International Application No. EP 15 19 0643.5 dated Feb. 26, 2016.
Extended European Search Report corresponding to International Application No. EP 15 16 6899.3 dated Feb. 3, 2016.
Extended European Search Report corresponding to International Application No. EP 14 19 9783.3 dated Dec. 22, 2015.
Extended European Search Report corresponding to International Application No. EP 15 17 3807.7 dated Nov. 24, 2015.
Extended European Search Report corresponding to International Application No. EP 15 19 0760.7 dated Apr. 1, 2016.
Extended European Search Report corresponding to International Application No. EP 15 17 3803.6 dated Nov. 24, 2015.
Extended European Search Report corresponding to International Application No. EP 15 17 3804.4 dated Nov. 24, 2015.
Extended European Search Report corresponding to International Application No. EP 15 18 8539.9 dated Feb. 17, 2016.
Extended European Search Report corresponding to International Application No. EP 15 17 3910.9 dated Nov. 13, 2015.
European Office Action corresponding to International Application No. EP 14 15 2236.7 dated Aug. 11, 2015.
Extended European Search Report corresponding to International Application No. EP 15 18 4915.5 dated Jan. 5, 2016.
Chinese Office Action corresponding to counterpart Int'l Appln. No. CN 201310369318.2 dated Jun. 28, 2016.
Chinese Office Action (with English translation), dated Jul. 4, 2016, corresponding to Chinese Patent Application No. 2015101559718; 23 total pages.
European Search Report EP 15 156 035.6 dated Aug. 10, 2016.
European Search Report corresponding to EP 15 184 915.5-1654 dated Sep. 16, 2016.
Australian Examination Report No. 1 corresponding to International Application No. AU 2013205872 dated Oct. 19, 2016.
Australian Examination Report from Appl. No. AU 2013205840 dated Nov. 3, 2016.
Notification of Transmittal of the International Search Report and The Written Opinion of the International Searching Authority issued in corresponding application No. PCT/US2016/027042 dated Jul. 12, 2016.
Extended European Search Report dated Feb. 2, 2022 corresponding to counterpart Patent Application EP 21195347.6.

* cited by examiner

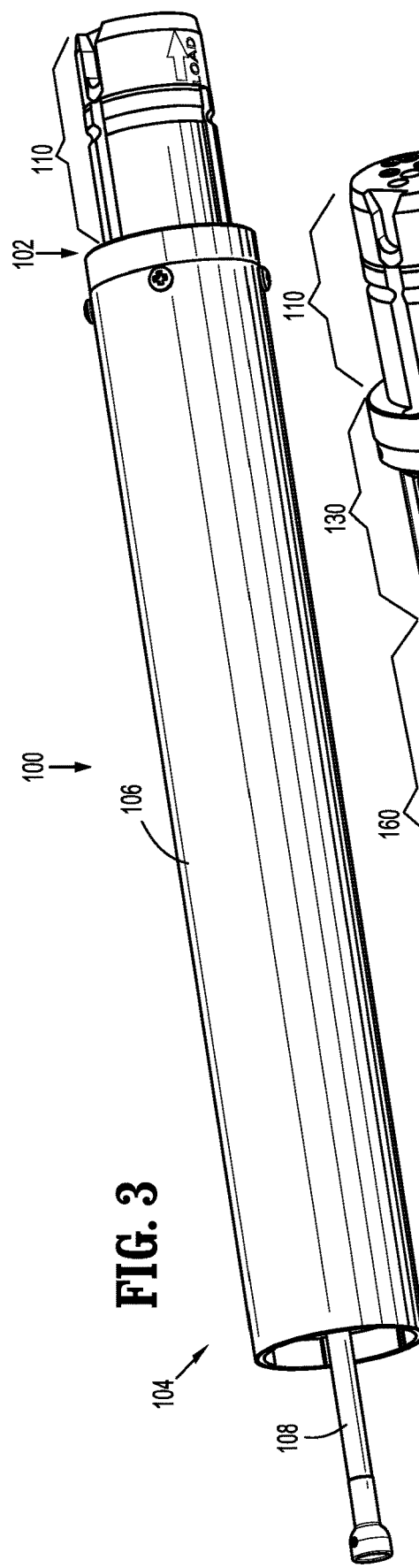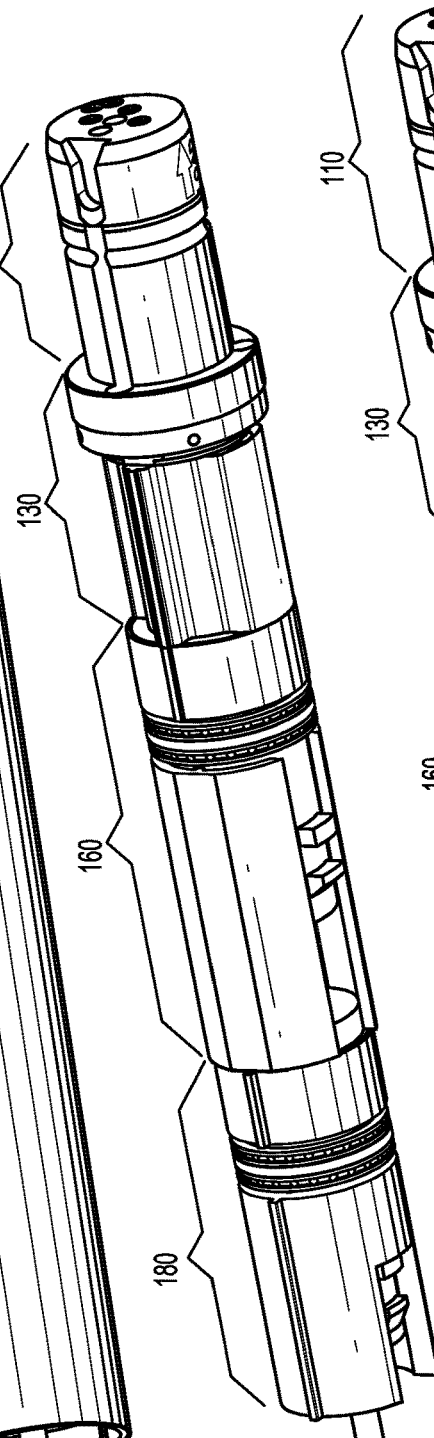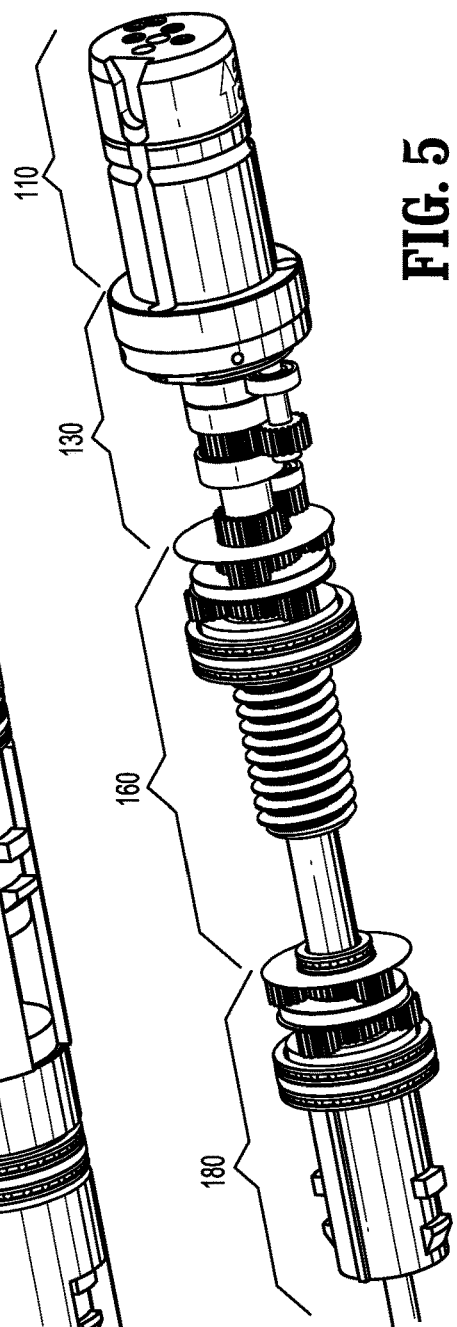

SURGICAL DEVICE WITH SEAL ASSEMBLY

CROSS-REFERENCE TO RELATED APPLICATION

This application claims the benefit of and priority to U.S. Provisional Patent Application No. 63/075,349, filed on Sep. 8, 2020, the entire contents of which are incorporated by reference herein.

BACKGROUND

The disclosure relates generally to surgical devices. More specifically, the disclosure relates to surgical devices with a seal assembly to limit the amount of debris that can enter the surgical device during use.

BACKGROUND OF RELATED ART

Surgical instruments including powered devices for use in surgical procedures are known. To permit reuse of the handle assemblies of these surgical instruments and so that the handle assembly may be used with a variety of end effectors, adapter assemblies and extension assemblies have been developed for selective attachment to the handle assemblies and to a variety of end effectors. Additionally, following use, the adapter, end effector and/or extension assemblies may be thoroughly cleaned and/or sterilized for reuse. A surgical device with a seal assembly may be helpful to limit the debris that enters the surgical device during use, and thereby facilitate cleaning of the surgical device.

SUMMARY

The disclosure relates to a surgical device including a handle assembly, an elongated portion configured to extend distally from the handle assembly and including an outer sleeve, an outer band assembly, an inner band assembly, a trocar assembly, and a seal assembly. At least a portion of the outer band assembly is disposed radially within the outer sleeve. At least a portion of the inner band assembly is disposed radially within the outer band assembly. The trocar assembly includes a trocar member. At least a portion of the trocar assembly is disposed radially within the inner band assembly. The seal assembly includes a first annular seal and a second annular seal. The first annular seal is disposed radially inward of the outer sleeve and radially outward of the outer band assembly. The second annular seal is disposed radially inward of the outer band assembly and radially outward of the inner band assembly.

In aspects, the seal assembly includes a third annular seal disposed radially inward of the inner band assembly and radially outward of the trocar member of the trocar assembly.

In aspects, the outer band assembly is longitudinally translatable relative to the outer sleeve of the elongated portion, and that the inner band assembly is longitudinally translatable relative to the outer band assembly and relative to the outer sleeve of the elongated portion. Further, in aspects, the inner band assembly is longitudinally translatable relative to the trocar member of the trocar assembly. In aspects, longitudinal movement of the outer band assembly relative to the outer sleeve of the elongated portion causes a corresponding longitudinal movement of the second annular seal relative to the outer sleeve.

Additionally, in aspects, the second annular seal is longitudinally translatable relative to the outer sleeve.

In aspects, the surgical device includes an end effector configured to operatively engage a distal portion of the elongated portion, and the end effector is configured to house fasteners therein. In aspects, that longitudinal movement of the outer band assembly relative to the outer sleeve of the elongated portion causes fasteners to be ejected from the end effector. In aspects, longitudinal movement of the inner band assembly relative to the outer sleeve of the elongated portion causes longitudinal movement of a knife of the end effector. In aspects, the end effector includes a cartridge assembly and an anvil assembly, and that longitudinal movement of a portion of the trocar assembly relative to the outer sleeve of the elongated portion causes longitudinal movement of the anvil assembly relative to the cartridge assembly.

In aspects, the first annular seal is between about 12 mm and about 100 mm from a distal-most end of the elongated portion, the second annular seal is between about 12 mm and about 100 mm from the distal-most end of the elongated portion, and the third annular seal is between about 12 mm and about 100 mm from the distal-most end of the elongated portion.

In aspects, the second annular seal is disposed at least partially within a recess of the outer band assembly. In further aspects, the third annular seal is disposed at least partially within a recess of the trocar member.

The disclosure also relates to a surgical device including an elongated portion having an outer sleeve, an outer band assembly, an inner band assembly, a trocar assembly, a seal assembly, and an end effector. The outer band assembly includes a first band and a second band, and at least a portion of the outer band assembly is disposed radially within the outer sleeve. The inner band assembly includes a first band and a second band, and at least a portion of the inner band assembly is disposed radially within the outer band assembly. The trocar assembly includes a trocar member, and at least a portion of the trocar assembly is disposed radially within the inner band assembly. The seal assembly includes a first seal, a second seal, and a third seal. The first seal is disposed radially inward of the outer sleeve and radially outward of the first band and the second band of the outer band assembly. The second seal is disposed radially inward of the first band and the second band of the outer band assembly and radially outward of the first band and the second band of the inner band assembly. The third seal is disposed radially inward of the first band and the second band of the inner band assembly and radially outward of the trocar member of the trocar assembly. The end effector is configured to operatively engage a distal portion of the elongated portion, and is configured to house fasteners therein. Distal movement of the outer band assembly relative to the outer sleeve causes fasteners to be ejected from the end effector, and distal movement of the inner band assembly relative to the outer sleeve causes distal movement of a knife of the end effector.

In aspects, the first seal is between about 12 mm and about 100 mm from a distal-most end of the elongated portion, the second seal is between about 12 mm and about 100 mm from the distal-most end of the elongated portion, and the third seal is between about 12 mm and about 100 mm from the distal-most end of the elongated portion.

In aspects, distal movement of the outer band assembly relative to the outer sleeve of the elongated portion causes a corresponding distal movement of the second seal relative to the outer sleeve.

BRIEF DESCRIPTION OF THE DRAWINGS

Aspects of the disclosure are described herein with reference to the accompanying drawings, wherein:

FIG. 3 is a perspective side view of and adapter assembly of the surgical device FIG. 1;

FIG. 4 is a perspective side view of the adapter assembly of FIG. 3 with an outer sleeve removed;

FIG. 5 is a perspective side view of the adapter assembly of FIGS. 3 and 4 with proximal and distal housings of first and second pusher assemblies removed;

DETAILED DESCRIPTION

Figure 1:
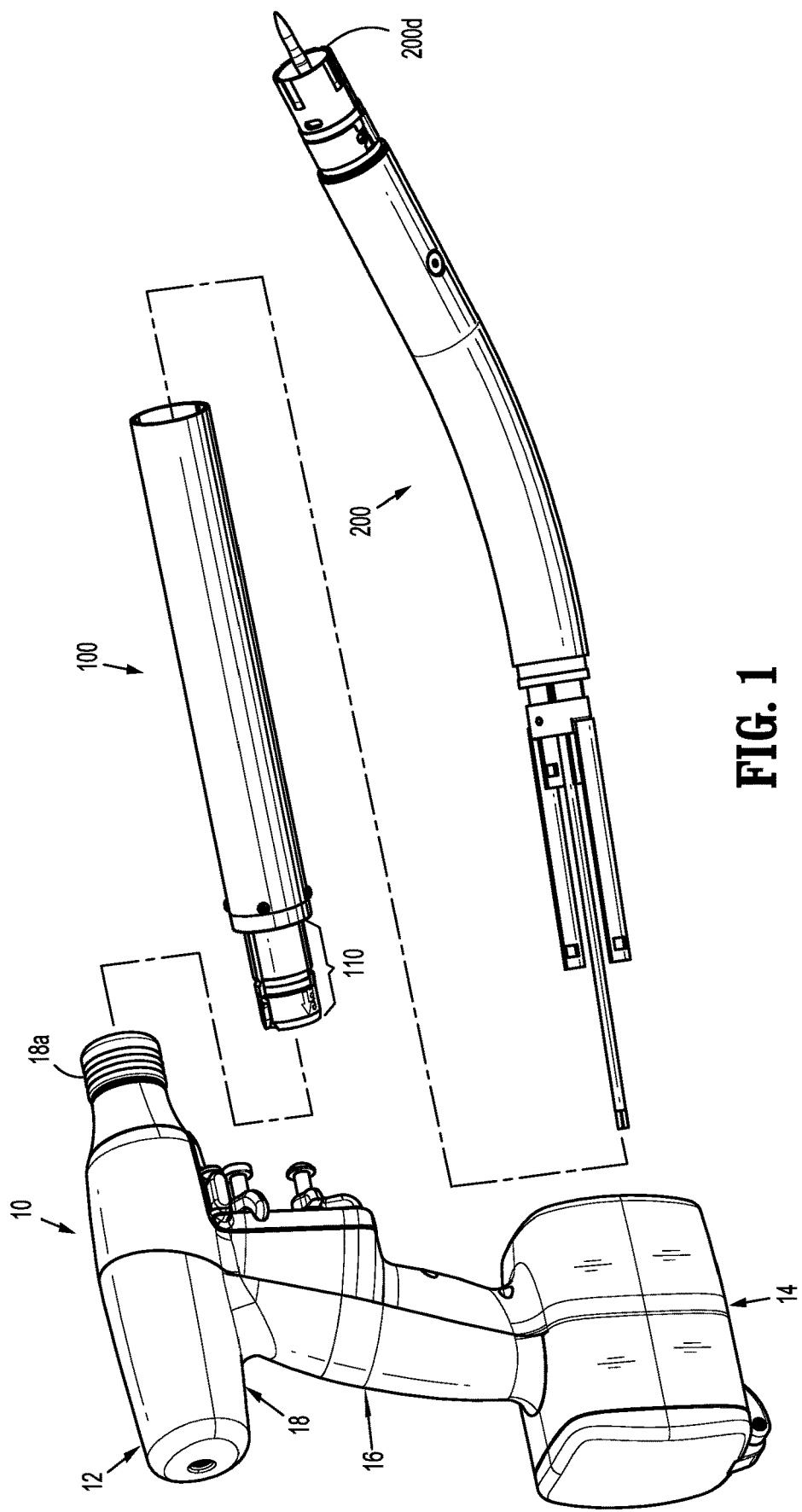
FIG. 1 is a perspective separated view of a surgical device in accordance with an aspect of the disclosure.

Aspects of the disclosed surgical device with a seal assembly are described in detail with reference to the drawings, in which like reference numerals designate identical or corresponding elements in each of the several views. As used herein the term "distal" refers to that portion of the seal assembly or surgical device, or component thereof, farther from the user, while the term "proximal" refers to that portion of the seal assembly or surgical device, or component thereof, closer to the user.

With reference to FIG. 1, an adapter assembly in accordance with an aspect of the disclosure, shown generally as adapter assembly 100, and an extension assembly according to an aspect of the disclosure, shown generally as extension assembly 200, are configured for selective connection to a powered handheld electromechanical instrument shown, generally as surgical device 10. As illustrated in FIG. 1, surgical device 10 is configured for selective connection with adapter assembly 100, and, in turn, adapter assembly 100 is configured for selective connection with an extension assembly 200. Extension assembly 200 is configured for selective connection with a tool assembly or end effector, e.g. tool assembly 30 (FIG. 12), including a loading unit, e.g. loading unit 40 (FIG. 12), and an anvil assembly, e.g., anvil assembly 50 (FIG. 12), for applying a circular array of staples (not shown) to tissue (not shown).

Figure 2:
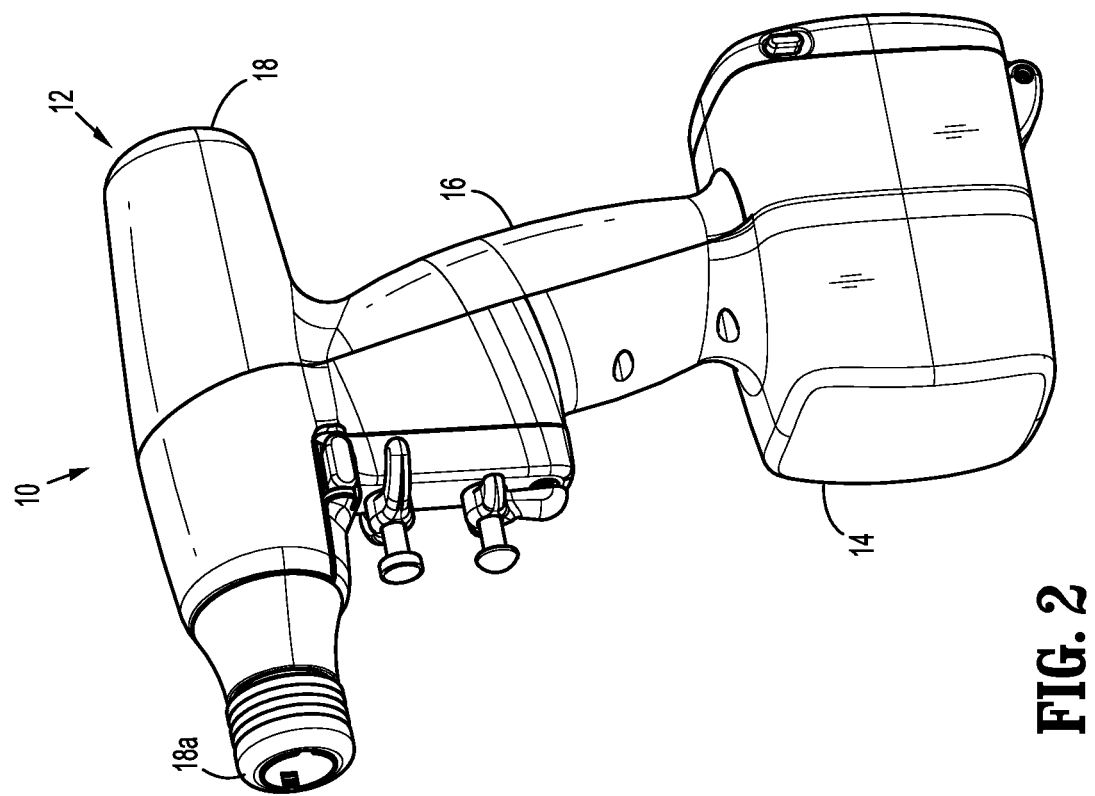
FIG. 2 is a perspective side view of a handle assembly of the surgical device of FIG. 1.

As illustrated in FIGS. 1 and 2, surgical device 10 includes a handle housing 12 having a lower housing portion 14, an intermediate housing portion 16 extending from and/or supported on lower housing portion 14, and an upper housing portion 18 extending from and/or supported on intermediate housing portion 16. A distal half-section of upper housing portion 18 defines a nose or connecting portion 18a configured to accept a corresponding drive coupling assembly 110 (FIGS. 3-5) of adapter assembly 100. For a detailed description of the structure and function of an exemplary electromechanical instrument, please refer to commonly owned U.S. Pat. No. 9,055,943, the contents of which is incorporated by reference herein in its entirety.

Adapter assembly 100 will now be described with reference to FIGS. 3-9. Referring initially to FIG. 3, adapter assembly 100 includes a proximal end 102 configured for operable connection to connecting portion 18a (FIG. 1) of surgical device 10 (FIG. 1) and a distal end 104 configured for operable connection to extension assembly 200 (FIG. 1). In accordance with the disclosure, adapter assembly 100 may be substantially or fully rigid along the entire length.

With specific reference to FIGS. 3-5, from proximal end 102 to distal end 104 of adapter assembly 100, adapter assembly 100 includes drive coupling assembly 110, a drive transfer assembly 130 operably connected to drive coupling assembly 110, a first pusher assembly 160 operably connected to drive transfer assembly 130, and a second pusher assembly 180 operably connected to drive transfer assembly 130. Each of drive transfer assembly 130, first pusher assembly 160 and second pusher assembly 180 are operably maintained within an outer sleeve 106 (FIG. 3). A shaft 108 (FIG. 3) extends longitudinally through adapter assembly 100 and is operably connected to drive transfer assembly 130.

Turning now to FIGS. 6-12, extension assembly 200 for operably connecting adapter assembly 100 (FIG. 3) with a circular loading unit, e.g. loading unit 40 (FIG. 12) and an anvil assembly, e.g., anvil assembly 50 (FIG. 12) will be described. In particular, a proximal end 202 of extension assembly 200 operably connects with distal end 104 (FIG. 3) of adapter assembly 100 (FIG. 3). A distal end 204 of extension assembly 200 operably connects with loading unit 40 and anvil assembly 50. As shown, extension assembly 200 provides a slight curvature between the proximal end 202 and the distal end 204. In an alternative aspect, extension assembly 200 may be straight or may include a greater or smaller curvature. In accordance with the disclosure, extension assembly 200 may be substantially or fully rigid along its entire length.

Although extension assembly 200 will be shown and described as being used to connect loading unit 40 and anvil assembly 50 to adapter assembly 100 (FIG. 3), it is envisioned that the aspects of the disclosure may be modified for use with various loading units, anvil assemblies, and adapter assemblies. Exemplary loading units and anvil assemblies are described in commonly-owned U.S. Pat. Nos. 8,590,763, 9,579,099, 10,463,365, the contents of each being incorporated herein by reference in their entirety. Additional exemplary surgical devices including flexible band assemblies are described in commonly-owned U.S. patent application Ser. No. 16/826,928, filed on Mar. 23, 2020 (now U.S. Patent Publication No. 2020-0214793), the contents being incorporated herein by reference in its entirety.

Extension assembly 200 includes an inner flexible band assembly 210 (FIG. 7), an outer flexible band assembly 230 (FIG. 8) slidably disposed about inner flexible band assembly 210, a frame assembly 250 (FIG. 9) for supporting inner and outer flexible band assemblies 210, 230, and a trocar assembly 270 (FIG. 11) operably received through inner and outer flexible band assemblies 210, 230. An outer sleeve 206 (FIG. 6) is received about frame assembly 250 and trocar assembly 270, and inner and outer flexible band assemblies 210, 230, respectively, are slidably received through outer sleeve 206. Extension assembly 200 may include a drive shaft 208 (FIG. 6) operably connected to trocar assembly 270 and extending through proximal end 202 of extension assembly 200.

Figure 6:
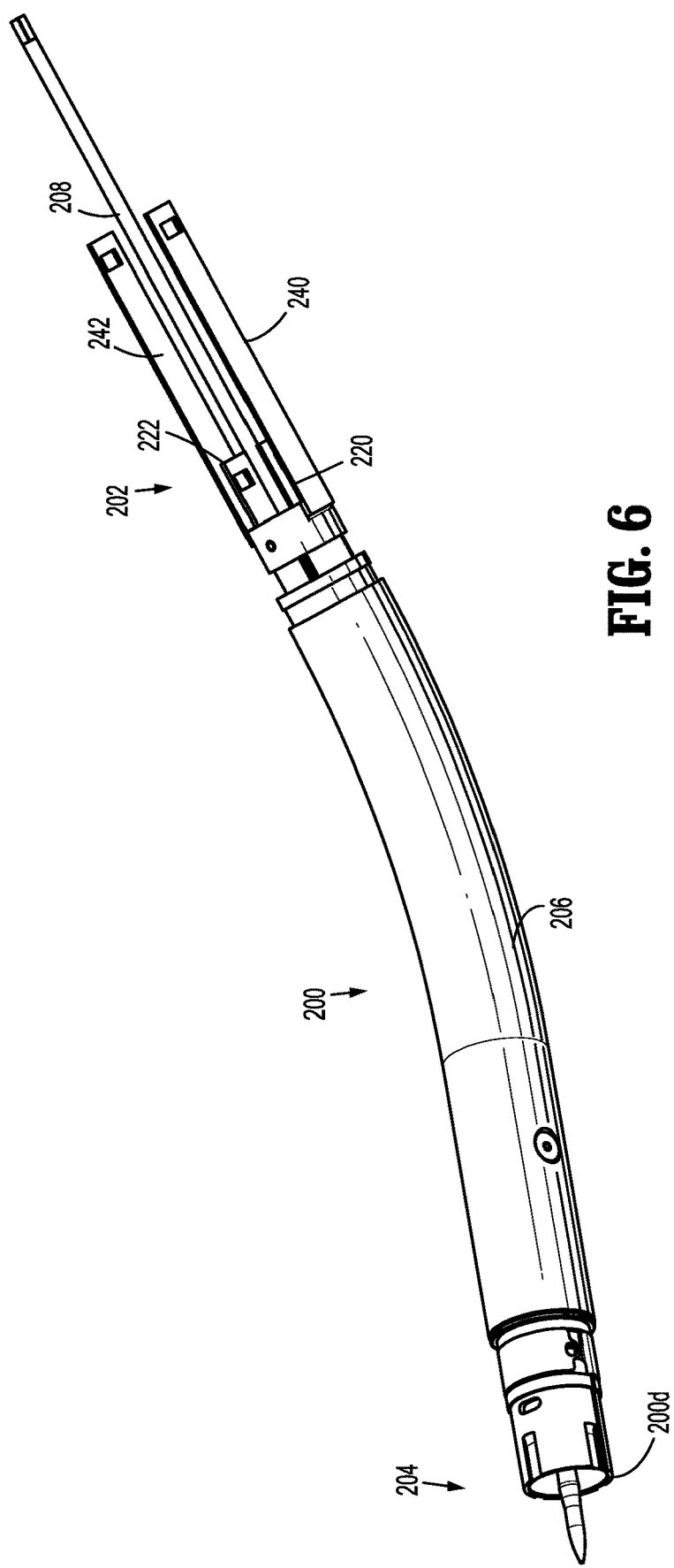
FIG. 6 is a perspective side view of an extension assembly of the surgical device of FIG. 1.
Figure 7:
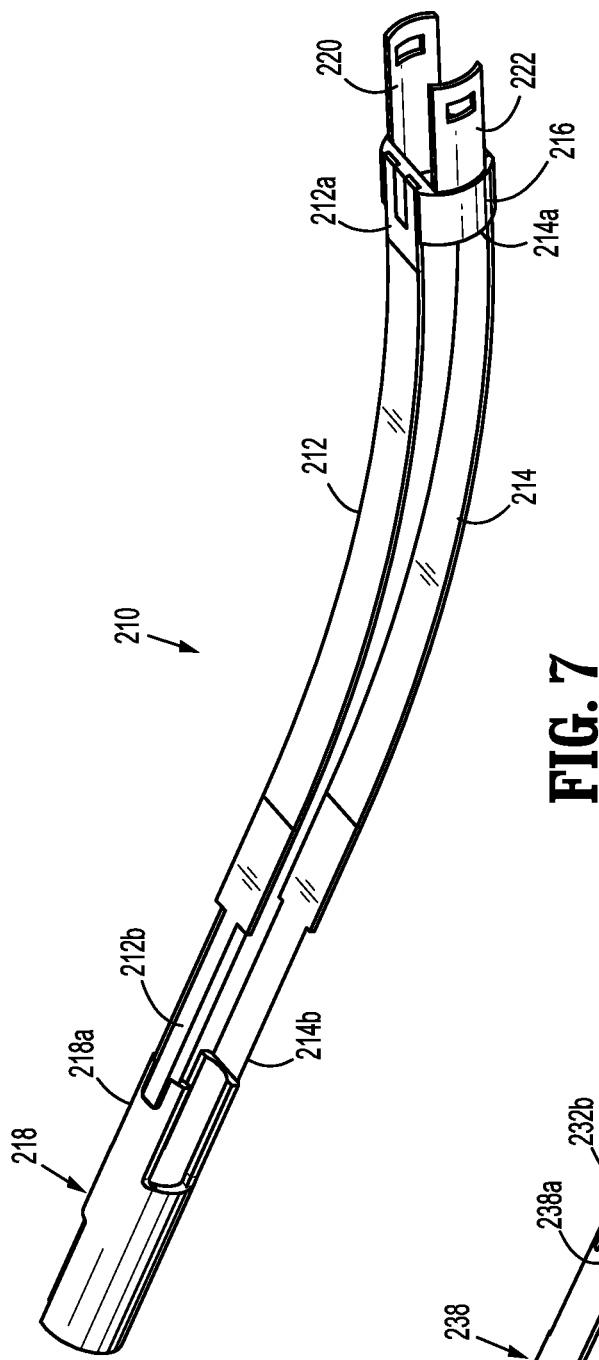
FIG. 7 is a perspective side view of an inner flexible band assembly of the extension assembly of FIG. 6.

With reference to FIG. 7, inner flexible band assembly 210 includes first and second inner flexible bands 212, 214, a support ring 216, a support base 218, and first and second connection extensions 220, 222. Proximal ends 212*a*, 214*a* of respective first and second inner flexible bands 212, 214 are laterally spaced apart and securely attached to support ring 216. Distal ends 212*b*, 214*b* of first and second inner flexible bands 212, 214 are laterally spaced apart and securely attached to a proximal end 218*a* of support base 218. Each of first and second inner flexible bands 212, 214 may be attached to support ring 216 and/or support base 218 in any suitable manner, including, for example, by press-fitting, welding, adhesives, and/or with mechanical fasteners. Inner flexible band assembly 210 is configured to be slidably received about trocar assembly 270 (FIG. 11) and within outer flexible band assembly 230 (FIG. 8) and outer sleeve 206 (FIG. 6).

Figure 8:
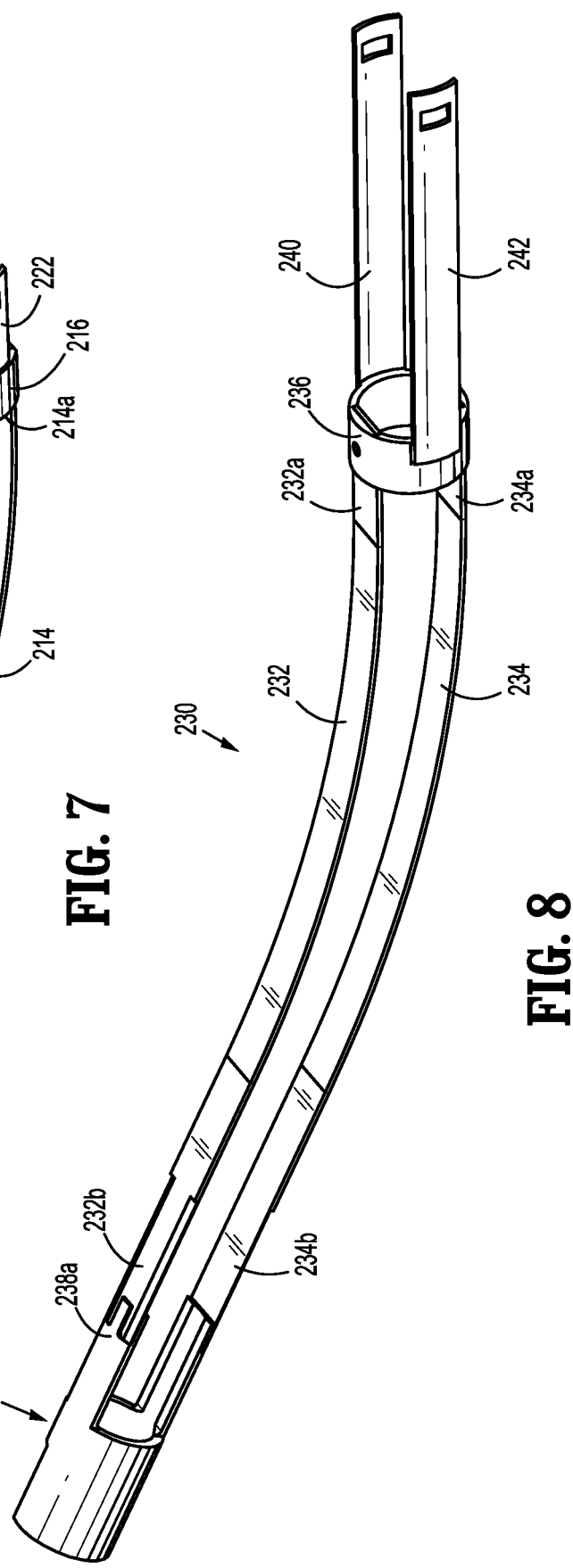
FIG. 8 is a perspective side view of an outer flexible band assembly of the extension assembly of FIG. 6.
Figure 9:
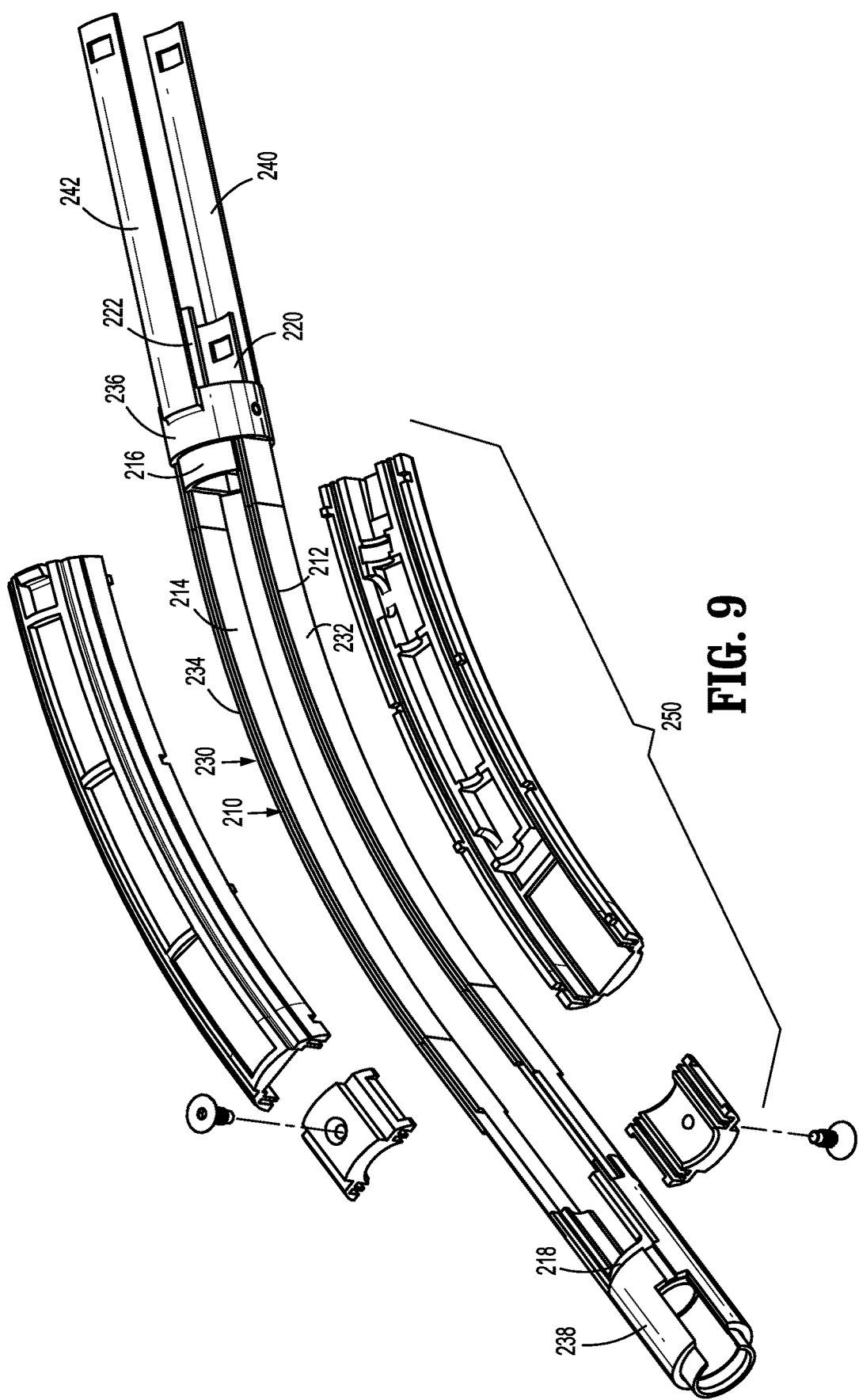
FIG. 9 is a perspective side view of the inner and outer flexible band assemblies of FIGS. 7 and 8 and an exploded view of a frame assembly of the extension assembly of FIG. 6.
Figure 10:
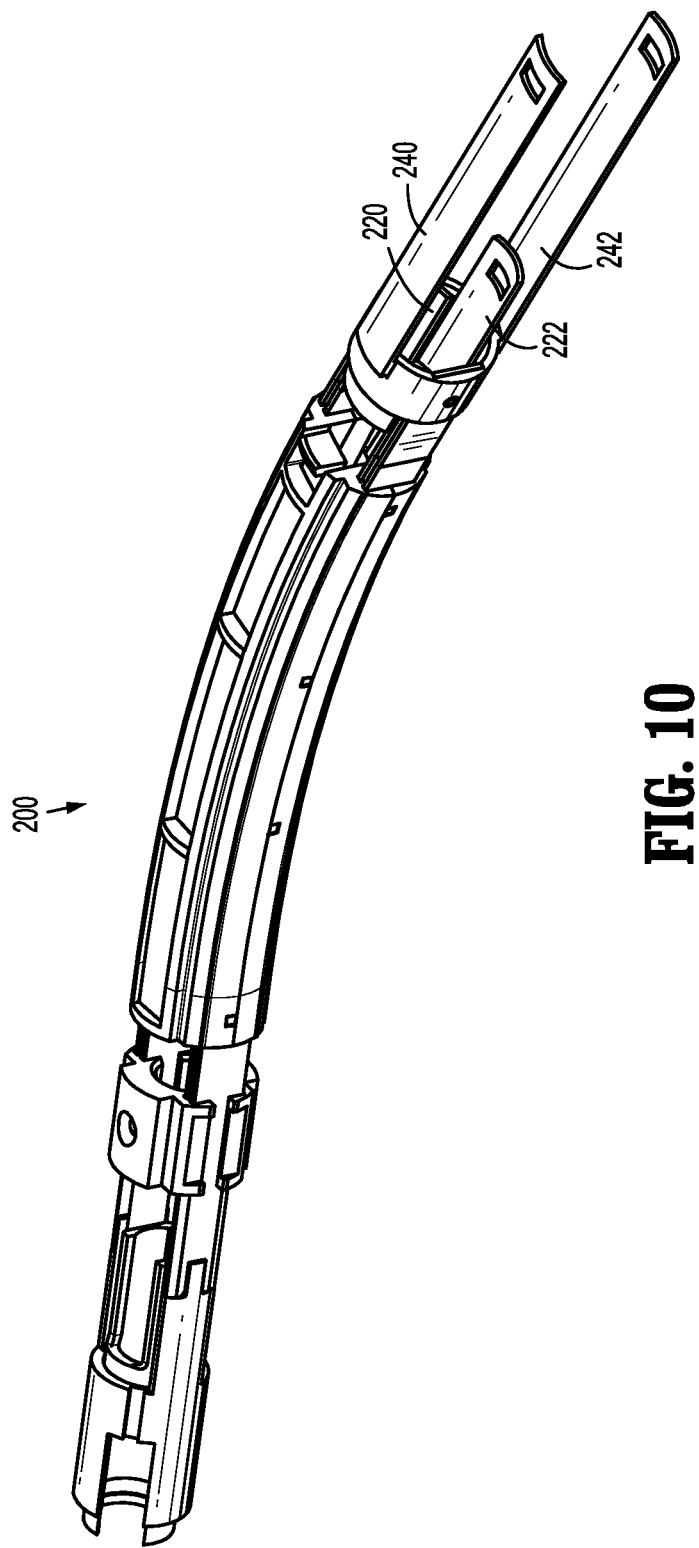
FIG. 10 is a perspective side view of the inner and outer flexible band assemblies and the frame assembly of FIG. 9.

With reference now to FIG. 8, outer flexible band assembly 230 is substantially similar to inner flexible band assembly 210 and includes first and second flexible bands 232, 234 laterally spaced and connected on proximal ends 232*a*, 234*a* to a support ring 236 and on distal ends 234*b*, 234*b* to a proximal end 238*a* of a support base 238. Each of first and second outer flexible bands 232, 234 may be attached to support ring 236 and support base 238 in any suitable manner, including, for example, by press-fitting, welding, adhesives, and/or with mechanical fasteners. Outer flexible band assembly 230 is configured to receive trocar assembly 270 (FIG. 11) therethrough.

First and second connection extensions 240, 242 of outer flexible band assembly 230 extend proximally from support ring 236 and operably connect outer flexible band assembly 230 with a pusher member of the first pusher assembly 160 (FIGS. 4 and 5) of adapter assembly 100 (FIGS. 1 and 3). First and second connection extensions 240, 242 may be integrally formed with support ring 236, or attached thereto in any suitable manner.

Figure 11:
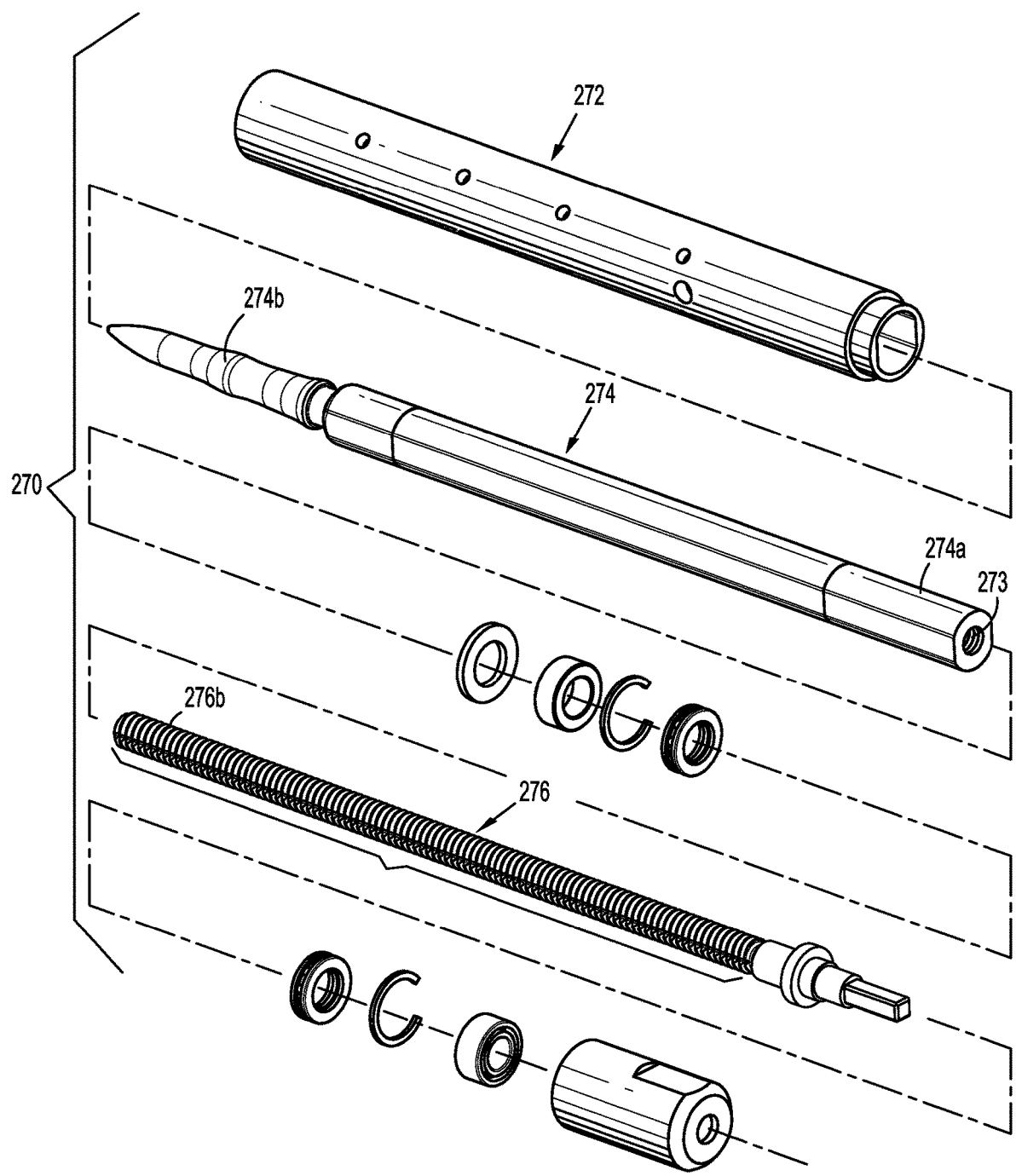
FIG. 11 is an exploded view of a trocar assembly of the extension assembly of FIG. 6.

With reference to FIG. 11, trocar assembly 270 of extension assembly 200 includes an outer housing 272, a trocar member 274 slidably disposed within tubular outer housing 272, and a drive screw 276 operably received within trocar member 274 for axially moving trocar member 274 relative to outer housing 272. In particular, trocar member 274 includes a proximal end 274*a* having an inner threaded portion 273 which engages a threaded distal portion 276*b* of drive screw 276. As drive screw 276 is rotated within trocar member 274, engagement between inner threaded portion 273 of trocar member 274 and threaded distal portion 276*b* of drive screw 276 causes longitudinal movement of trocar member 274 relative to the outer housing 272 of trocar assembly 270. Rotation of drive screw 276 in a first direction causes distal advancement of trocar member 274 and rotation of drive screw 276 in a second direction causes proximal retraction of trocar member 274. A distal end 274*b* of trocar member 274 is configured to selectively engage anvil assembly 50 (FIG. 12).

After extension assembly 200 is operably engaged with adapter assembly 100, and adapter assembly 100 is operably engaged with surgical device 10 (FIG. 1), loading unit 40 (FIG. 12) of end effector 30 (FIG. 12) may be attached to extension assembly 200 and an anvil assembly 50 (FIG. 12) may be attached to or engaged with a distal end 274*b* of trocar member 274 of extension assembly 200 in a conventional manner. During actuation of loading unit 40 and anvil assembly 50, longitudinal advancement of a pusher member of second pusher assembly 180 of adapter assembly 100, as described above, and as indicated by arrows "C" in FIG. 13, causes longitudinal advancement of outer flexible band assembly 230 of extension assembly 200. Longitudinal advancement of the pusher member of the first pusher assembly 160, and as indicated by arrows "D" in FIG. 13, causes longitudinal advancement of inner flexible band assembly 210. Rotation of drive shaft 108 in a first direction, and as indicated by arrow "E" in FIG. 13, causes advancement of the trocar member 274 of extension assembly 200. Conversely, proximal retraction of the pusher member of the second pusher assembly 180 causes proximal retraction of outer flexible band assembly 230, and proximal retraction of the pusher member of the first pusher assembly 160 causes proximal retraction of inner flexible band assembly 210. Additionally, rotation of drive shaft 108 in a second direction causes retraction of the trocar member 274 of extension assembly 200.

Figure 12:
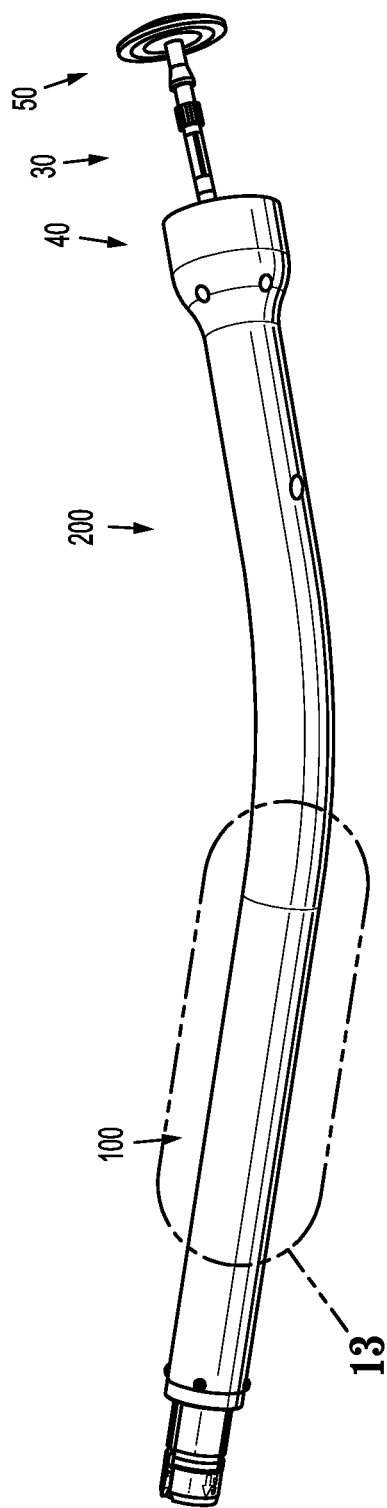
FIG. 12 is a perspective side view of the adapter assembly of FIG. 3 connected to the extension assembly of FIG. 6 and an end effector and an anvil assembly engaged with the extension assembly.
Figure 13:
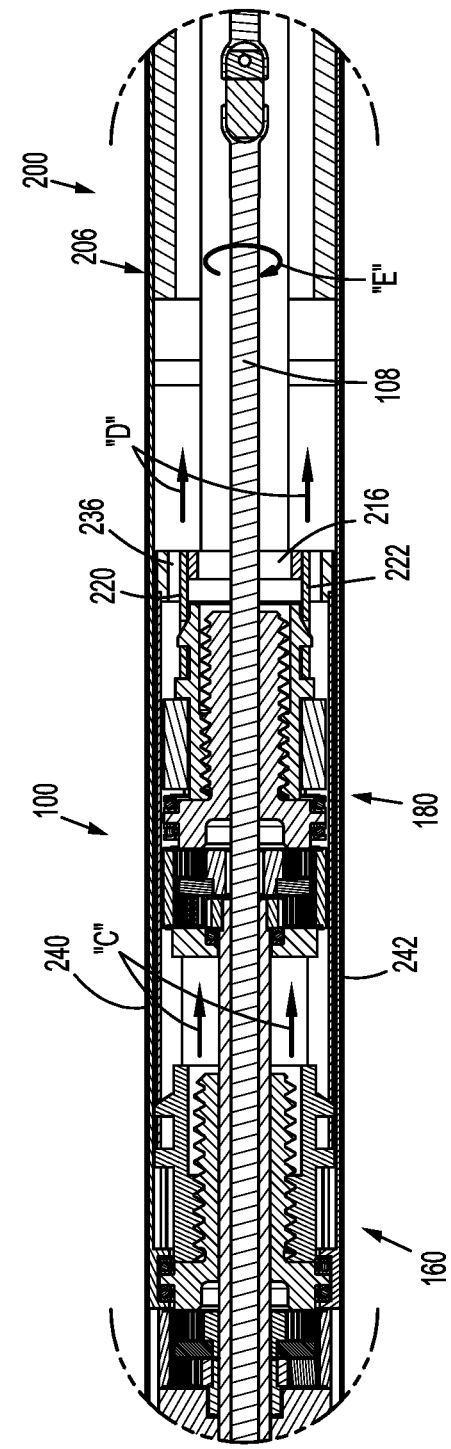
FIG. 13 is an enlarged cross-sectional side view of the indicated area of detail of FIG. 12.

Inner flexible band assembly 210 is operably connected to a knife assembly (not show) of loading unit 40 of end effector 30 (FIG. 12), outer flexible band assembly 230 is operably connected to a staple driver assembly (not shown) of loading unit 40, and trocar member 274 is operably connected to anvil assembly 50 of end effector 30 (FIG. 12). In this manner, longitudinal movement of inner flexible band assembly 210 causes longitudinal movement of the knife assembly (e.g., to cut tissue), longitudinal movement of outer flexible band assembly 230 causes longitudinal movement of the staple driver assembly (e.g., to emplace fasteners into tissue), and longitudinal movement of trocar member 274 causes longitudinal movement of anvil assembly 50 relative to loading unit 40 (e.g., to grasp tissue therebetween).

Figure 14:
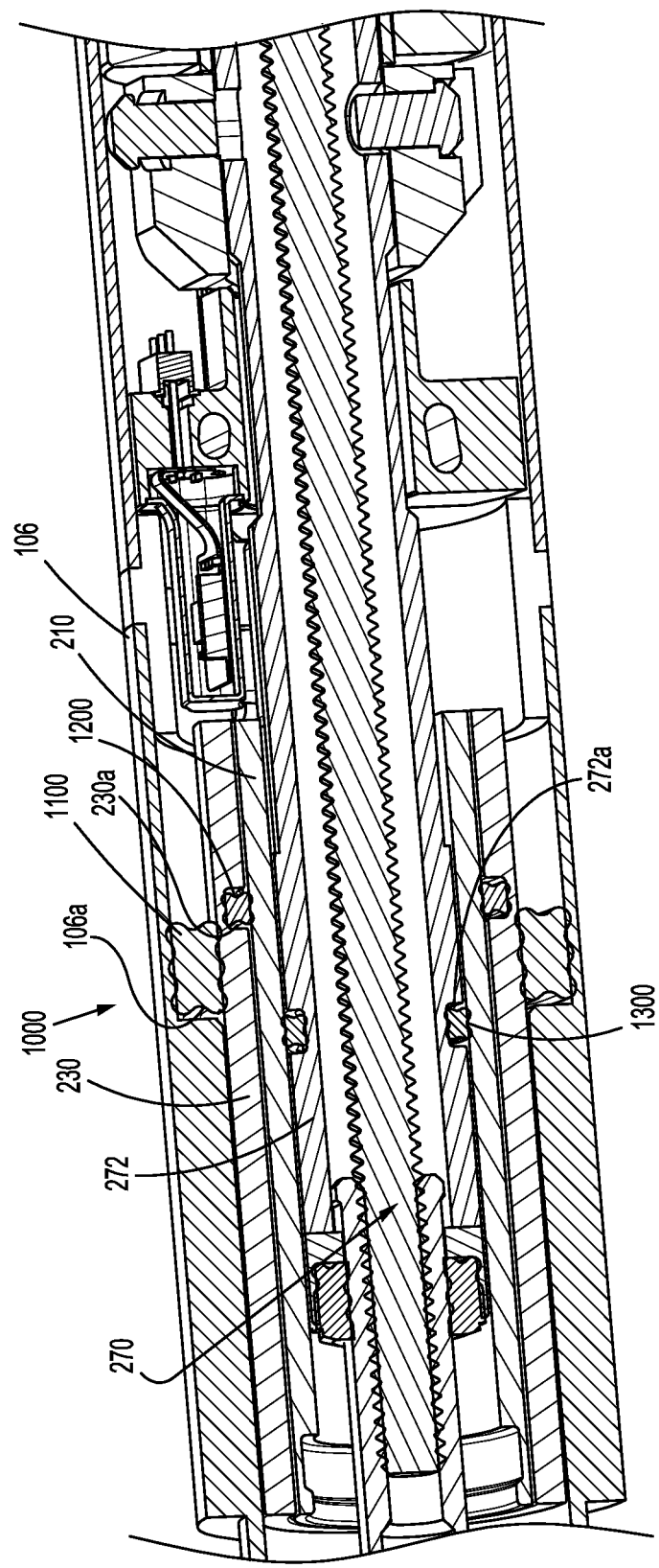
FIG. 14 is a cross-sectional view of a distal portion of the extension assembly of FIG. 6.

Referring now to FIG. 14, a seal assembly 1000 for use with surgical device 10, adapter assembly 100, and/or extension assembly 200 of the disclosure is shown. Seal assembly 1000 is configured to facilitate thoroughly cleaning debris (e.g., surgical debris) from surgical device 10 following use, prior to use, and/or prior to reuse, for instance. Further, seal assembly 1000 is configured to prevent or minimize fluid, soil and debris from travelling proximally beyond the seal assembly 1000 after the fluid, soil and debris has entered the surgical device 10 from at or near a distal end thereof. That is, since the seal assembly 1000 is located relatively close to the distal end of the surgical device 10, the area of the surgical device 10 (e.g., within the outer sleeve 106) that is exposed to fluid, soil and debris is relatively small and easily cleaned. Additionally, while seal assembly 1000 is shown and described for use a particular type of surgical device 10, seal assembly 1000 is usable with various types of surgical instruments (e.g., reusable) where cleaning and/or sterilization may be desired.

Seal assembly 1000 includes a first seal 1100, a second seal 1200, and a third seal 1300. The first seal 1100 is an annular seal and is positioned between the outer sleeve 106 and the outer flexible band assembly 230, and is configured to hinder or prevent fluid from travelling between the outer sleeve 106 and the outer flexible band assembly 230 to a location that is proximal of the first seal 1100. More particularly the first seal 1100 is positioned radially inwardly of the outer sleeve 106 (or portions thereof), and radially outwardly of the outer flexible band assembly 230 (or portions thereof) of the extension assembly 200. Further the outer sleeve 106 includes a recess or notch 106a therein configured to help prevent the first seal 1100 from moving distally relative to the outer sleeve 106.

The second seal 1200 of the seal assembly 1000 is positioned between the outer flexible band assembly 230 of the extension assembly 200, and the inner flexible band assembly 210 of the extension assembly 200, and is configured to hinder or prevent fluid from travelling between the inner flexible band assembly 210 and the outer flexible band assembly 230 to a location that is proximal of the second seal 1200. More particularly the second seal 1200 is positioned radially inwardly of the outer flexible band assembly 230, and radially outwardly of the inner flexible band assembly 210. Further the outer flexible band assembly 230 includes a recess 230a therein configured to retain the second seal 1200 at least partially therein in response to movement between the inner flexible band assembly 210 and the outer flexible band assembly 230.

The third seal 1300 of the seal assembly 1000 is positioned between the inner flexible band assembly 210 of the extension assembly 200 and the outer housing 272 of the trocar assembly 270, and is configured to hinder or prevent fluid from travelling between the inner flexible band assembly 210 and the outer housing 272 of the trocar assembly 270 to a location that is proximal of the third seal 1300. More particularly the third seal 1300 is positioned radially inwardly of the inner flexible band assembly 210, and radially outwardly of the outer housing 272 of the trocar assembly 270. Further the outer housing 272 of the trocar assembly 270 includes a recess 272a therein configured to retain the third seal 1300 at least partially therein in response to movement between the inner flexible band assembly 210 and the outer housing 272 of the trocar assembly 270.

As noted above, the relative distal location of the first seal 1100, the second seal 1200, and the third seal 1300 of the seal assembly 1000 help ensure that any fluid, soil and debris that enters the distal end of the surgical device 10 is a relatively small amount and easily cleaned. While the particular distances that first seal 1100, the second seal 1200, and the third seal 1300 are spaced from a distal-most end 10d of the surgical device 10 may vary without departing from the scope of the disclosure, it is envisioned that, prior to the surgical device 10 being actuated, the first seal 1100 is between about 12 mm and 100 mm from a distal-most end 200d of the extension assembly 200 (FIGS. 1 and 6), the second seal 1200 is between about 12 mm and 100 mm from the distal-most end 200d of the extension assembly 200, and the third seal 1300 is between about 12 mm and 100 mm from the distal-most end 200d of the extension assembly 200.

During use of the surgical device 10, the second seal 1200 of the seal assembly 1000 is configured to move longitudinally. In particular, when the outer flexible band assembly 230 translates longitudinally relative to the outer sleeve 106 and/or relative to the inner flexible band assembly 210 (e.g., to cause staples to be ejected from the surgical device 10), as discussed above, the second seal 1200, which is retained by the recess 230a of the outer flexible band assembly 230, also translates longitudinally. Due to the engagement between the second seal 1200 and the inner flexible band assembly 210, the sealed relationship between the outer flexible band assembly 230 and the inner flexible band assembly 210, created by the second seal 1200, is maintained during longitudinal translation of the outer flexible band assembly 230 relative to the inner flexible band assembly 210. Further, the sealed relationship between the outer flexible band assembly 230 and the outer sleeve 106, created by the first seal 1100, is maintained during longitudinal translation of the outer flexible band assembly 230 relative to the inner flexible band assembly 210.

Additionally, when the inner flexible band assembly 210 translates longitudinally relative to the outer housing 272 of the trocar assembly 270 (e.g., to cause tissue to be severed), as discussed above, the third seal 1300, which is retained by the recess 272a of the outer housing 272, remains in its longitudinal position. Due to the engagement between the third seal 1300 and the inner flexible band assembly 210, created by the third seal 1300, the sealed relationship between the inner flexible band assembly 210 and the outer housing 272 of the trocar assembly 270 is maintained during longitudinal translation of the inner flexible band assembly 210 relative to the outer housing 272 of the trocar assembly 270.

Surgical devices such as those described herein may also be configured to work with robotic surgical systems and what is commonly referred to as "Telesurgery." Such systems employ various robotic elements to assist the surgeon and allow remote operation (or partial remote operation) of surgical instrumentation. Various robotic arms, gears, cams, pulleys, electric and mechanical motors, etc. may be employed for this purpose and may be designed with a robotic surgical system to assist the surgeon during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of surgeons or nurses may prep the patient for surgery and configure the robotic surgical system with one or more of the instruments disclosed herein while another surgeon (or group of surgeons) remotely control the instruments via the robotic surgical system. As can be appreciated, a highly skilled surgeon may perform multiple operations in multiple locations without leaving his/her remote console which can be both economically advantageous and a benefit to the patient or a series of patients.

The robotic arms of the surgical system are typically coupled to a pair of master handles by a controller. The handles can be moved by the surgeon to produce a corresponding movement of the working ends of any type of surgical instrument (e.g., end effectors, graspers, knifes, scissors, etc.) which may complement the use of one or more of the aspects described herein. The movement of the master handles may be scaled so that the working ends have a corresponding movement that is different, smaller or larger, than the movement performed by the operating hands of the surgeon. The scale factor or gearing ratio may be adjustable so that the operator can control the resolution of the working ends of the surgical instrument(s).

The master handles may include various sensors to provide feedback to the surgeon relating to various tissue parameters or conditions, e.g., tissue resistance due to manipulation, cutting or otherwise treating, pressure by the instrument onto the tissue, tissue temperature, tissue impedance, etc. As can be appreciated, such sensors provide the surgeon with enhanced tactile feedback simulating actual operating conditions. The master handles may also include a variety of different actuators for delicate tissue manipulation or treatment further enhancing the surgeon's ability to mimic actual operating conditions.

Figure 15:
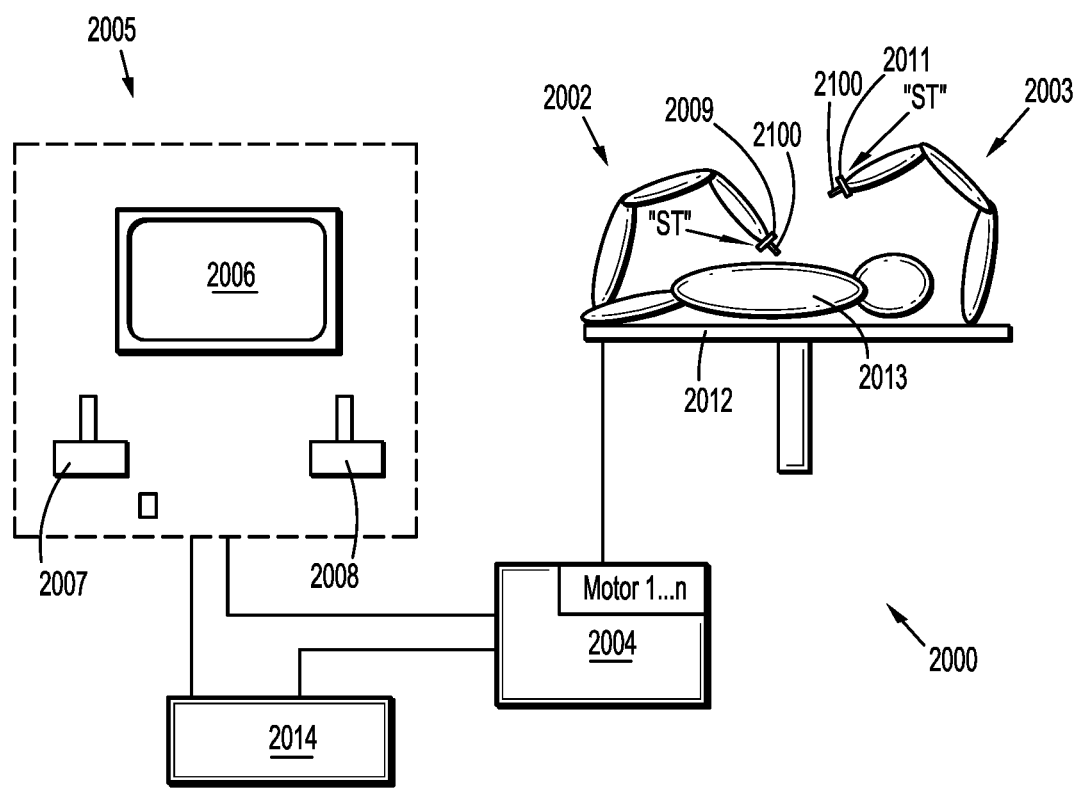
FIG. 15 is a schematic illustration of a robotic surgical system configured for use in accordance with the disclosure.

Referring to FIG. 15, a medical work station is shown generally as work station 2000 and generally may include a plurality of robot arms 2002, 2003; a control device 2004; and an operating console 2005 coupled with control device 2004. Operating console 2005 may include a display device 1006, which may be set up in particular to display three-dimensional images; and manual input devices 2007, 2008, by means of which a person (not shown), for example a surgeon, may be able to telemanipulate robot arms 2002, 2003 in a first operating mode.

Each of the robot arms 2002, 2003 may include a plurality of members, which are connected through joints, and an attaching device 2009, 2011, to which may be attached, for example, a surgical tool "ST" supporting an end effector 2100, in accordance with any one of several aspects disclosed herein, as will be described in greater detail below.

Robot arms 2002, 2003 may be driven by electric drives (not shown) that are connected to control device 1004. Control device 2004 (e.g., a computer) may be set up to activate the drives, in particular by means of a computer program, in such a way that robot arms 2002, 2003, their attaching devices 2009, 2011 and thus the surgical tool (including end effector 2100) execute a desired movement according to a movement defined by means of manual input devices 2007, 2008. Control device 2004 may also be set up in such a way that it regulates the movement of robot arms 2002, 2003 and/or of the drives.

Medical work station 2000 may be configured for use on a patient 2013 lying on a patient table 2012 to be treated in a minimally invasive manner by means of end effector 2100. Medical work station 2000 may also include more than two robot arms 2002, 2003, the additional robot arms likewise being connected to control device 2004 and being telemanipulatable by means of operating console 1005. A medical instrument or surgical tool (including an end effector 2100) may also be attached to the additional robot arm. Medical work station 2000 may include a database 2014, in particular coupled to with control device 2004, in which are stored, for example, pre-operative data from patient/living being 2013 and/or anatomical atlases.

Reference is made herein to U.S. Pat. No. 8,828,023 to Neff et al., entitled "Medical Workstation," the entire content of which is incorporated herein by reference, for a more detailed discussion of the construction and operation of an exemplary robotic surgical system.

Any of the components described herein may be fabricated from either metals, plastics, resins, composites or the like taking into consideration strength, durability, wearability, weight, resistance to corrosion, ease of manufacturing, cost of manufacturing, and the like.

It should be understood that the foregoing description is only illustrative of the disclosure. Various alternatives and modifications can be devised by those skilled in the art without departing from the disclosure. Accordingly, the disclosure is intended to embrace all such alternatives, modifications and variances. The aspects described with reference to the attached drawing figures are presented only to demonstrate certain examples of the disclosure. Other elements, steps, methods and techniques that are insubstantially different from those described above and/or in the appended claims are also intended to be within the scope of the disclosure.

What is claimed:

1. A surgical device comprising:
a handle assembly;
an elongated portion configured to extend distally from the handle assembly and including an outer sleeve;
an outer band assembly, at least a portion of the outer band assembly disposed radially within the outer sleeve;
an inner band assembly, at least a portion of the inner band assembly disposed radially within the outer band assembly;
a trocar assembly including a trocar member and an outer housing disposed radially outward of at least a portion of the trocar member, the outer housing disposed radially within the inner band assembly; and
a seal assembly including:
a first annular seal, the first annular seal disposed radially inward of and in contact with the outer sleeve, and radially outward of and in contact with the outer band assembly,
a second annular seal, an entirety of the second annular seal disposed radially inward of the outer band assembly and radially outward of the inner band assembly, the second annular seal disposed within a recess of the outer band assembly and in contact with the inner band assembly such that longitudinal translation of the outer band assembly relative to the inner band assembly causes a corresponding longitudinal translation of the second annular seal relative to the inner band assembly, and
a third annular seal, an entirety of the third annular seal disposed radially inward of and in contact with the inner band assembly, the third annular seal disposed within a recess of the outer housing, wherein the third annular seal is configured to remain in its longitudinal position when the inner band assembly moves longitudinally relative to the outer housing.

2. The surgical device according to claim 1, wherein the third annular seal is disposed radially outward of the trocar member of the trocar assembly.

3. The surgical device according to claim 1, wherein the outer band assembly is longitudinally translatable relative to the outer sleeve of the elongated portion.

4. The surgical device according to claim 3, wherein the inner band assembly is longitudinally translatable relative to the outer sleeve of the elongated portion.

5. The surgical device according to claim 4, wherein the inner band assembly is longitudinally translatable relative to the trocar member of the trocar assembly.

6. The surgical device according to claim 3, wherein longitudinal movement of the outer band assembly relative to the outer sleeve of the elongated portion causes a corresponding longitudinal movement of the second annular seal relative to the outer sleeve.

7. The surgical device according to claim 1, wherein the second annular seal is longitudinally translatable relative to the outer sleeve.

8. The surgical device according to claim 1, further including an end effector configured to operatively engage a distal portion of the elongated portion, the end effector configured to house fasteners therein.

9. The surgical device according to claim 8, wherein longitudinal movement of the outer band assembly relative to the outer sleeve of the elongated portion causes fasteners to be ejected from the end effector.

10. The surgical device according to claim 8, wherein longitudinal movement of the inner band assembly relative to the outer sleeve of the elongated portion causes longitudinal movement of a knife of the end effector.

11. The surgical device according to claim 8, wherein the end effector includes a cartridge assembly and an anvil assembly, and wherein longitudinal movement of a portion of the trocar assembly relative to the outer sleeve of the elongated portion causes longitudinal movement of the anvil assembly relative to the cartridge assembly.

12. The surgical device according to claim 1, wherein the first annular seal is between about 12 mm and about 100 mm from a distal-most end of the elongated portion.

13. The surgical device according to claim 12, wherein the second annular seal is between about 12 mm and about 100 mm from the distal-most end of the elongated portion.

14. The surgical device according to claim 13, wherein the third annular seal is disposed radially outward of the trocar member of the trocar assembly, and wherein the third annular seal is between about 12 mm and about 100 mm from the distal-most end of the elongated portion.

15. A surgical device comprising:
an elongated portion including an outer sleeve;
an outer band assembly including a first band and a second band, at least a portion of the outer band assembly disposed radially within the outer sleeve;
an inner band assembly including a first band and a second band, at least a portion of the inner band assembly disposed radially within the outer band assembly;
a trocar assembly including a trocar member and an outer housing disposed radially outward of at least a portion of the trocar member, the outer housing disposed radially within the inner band assembly;
a seal assembly including:
a first annular seal, the first annular seal disposed radially inward of and in contact with the outer sleeve, and radially outward of and in contact with the first band and the second band of the outer band assembly,
a second annular seal, an entirety of the second annular seal disposed radially inward of the first band and the second band of the outer band assembly and radially outward of the first band and the second band of the inner band assembly, the second annular seal disposed within a recess of the outer band assembly and in contact with the inner band assembly such that longitudinal translation of the outer band assembly relative to the inner band assembly causes a corresponding longitudinal translation of the second annular seal relative to the inner band assembly, and
a third annular seal, an entirety of the third annular seal disposed radially inward of and in contact with the inner band assembly and radially outward of the trocar member of the trocar assembly, the third annular seal disposed within a recess of the outer housing, wherein the third annular seal is configured to remain in its longitudinal position when the inner band assembly moves longitudinally relative to the outer housing; and
an end effector configured to operatively engage a distal portion of the elongated portion, the end effector configured to house fasteners therein, wherein distal movement of the outer band assembly relative to the outer sleeve causes fasteners to be ejected from the end effector, and wherein distal movement of the inner band assembly relative to the outer sleeve causes distal movement of a knife of the end effector.

16. The surgical device according to claim 15, wherein the first annular seal is between about 12 mm and about 100 mm from a distal-most end of the elongated portion, wherein the second annular seal is between about 12 mm and about 100 mm from the distal-most end of the elongated portion, and wherein the third annular seal is between about 12 mm and about 100 mm from the distal-most end of the elongated portion.

17. The surgical device according to claim 15, wherein distal movement of the outer band assembly relative to the outer sleeve of the elongated portion causes a corresponding distal movement of the second annular seal relative to the outer sleeve.

* * * * *